(12) United States Patent
Chen et al.

(10) Patent No.: US 11,097,014 B2
(45) Date of Patent: Aug. 24, 2021

(54) METHODS FOR TREATING SUBJECTS SUFFERING FROM ACUTE MYELOID LEUKEMIA WITH FLT3 LIGAND-TARGETED MIR-150 NANOPARTICLES

(71) Applicants: University of Cincinnati, Cincinnati, OH (US); The Board of Trustees of the University of Illinois, Chicago, IL (US); The University of Chicago, Chicago, IL (US)

(72) Inventors: Jianjun Chen, Cincinnati, OH (US); Seungpyo Hong, Naperville, IL (US); Xi Jiang, Cincinnati, OH (US); Zejuan Li, Chicago, IL (US)

(73) Assignees: University of Cincinnati, Cincinnati, OH (US); Board of Trustees of the University of Illinois, Chicago, IL (US); University of Chicago, Chicago, IL (US)

( * ) Notice: Subject to any disclaimer, the term of this patent is extended or adjusted under 35 U.S.C. 154(b) by 102 days.

(21) Appl. No.: 16/310,104

(22) PCT Filed: Jun. 14, 2017

(86) PCT No.: PCT/US2017/037424
§ 371 (c)(1),
(2) Date: Dec. 14, 2018

(87) PCT Pub. No.: WO2017/218638
PCT Pub. Date: Dec. 21, 2017

(65) Prior Publication Data
US 2019/0175754 A1    Jun. 13, 2019

Related U.S. Application Data

(60) Provisional application No. 62/349,707, filed on Jun. 14, 2016.

(51) Int. Cl.
| | |
|---|---|
| *C12N 15/11* | (2006.01) |
| *A61K 47/69* | (2017.01) |
| *A61K 31/551* | (2006.01) |
| *A61P 35/02* | (2006.01) |
| *A61K 38/19* | (2006.01) |
| *A61K 45/06* | (2006.01) |
| *A61K 47/59* | (2017.01) |
| *A61K 47/62* | (2017.01) |
| *A61K 31/7105* | (2006.01) |
| *C12N 15/113* | (2010.01) |

(52) U.S. Cl.
CPC ........ *A61K 47/6935* (2017.08); *A61K 31/551* (2013.01); *A61K 31/7105* (2013.01); *A61K 38/19* (2013.01); *A61K 45/06* (2013.01); *A61K 47/595* (2017.08); *A61K 47/62* (2017.08); *A61P 35/02* (2018.01); *C12N 15/1138* (2013.01); *C12N 2310/141* (2013.01); *C12N 2310/321* (2013.01)

(58) Field of Classification Search
CPC ..................... C12N 15/1138; C12N 2310/141
See application file for complete search history.

(56) References Cited

U.S. PATENT DOCUMENTS

| | | | | |
|---|---|---|---|---|
| 5,554,512 | A * | 9/1996 | Lyman | A01K 67/0275 435/69.5 |
| 7,534,867 | B1 | 5/2009 | Hannum et al. | |
| 2009/0105174 | A1* | 4/2009 | Jayasena | C12N 15/113 514/44 R |
| 2014/0335192 | A1* | 11/2014 | Ward | C12N 15/87 424/499 |

FOREIGN PATENT DOCUMENTS

| | | | | |
|---|---|---|---|---|
| WO | WO-2014062135 A1 * | 4/2014 | | B32B 27/38 |
| WO | 2016107933 A2 | 7/2016 | | |

OTHER PUBLICATIONS

Jiang et al, Blockade of miR-150 Maturation by MLL-Fusion/MYC/LIN-28 Is Required for MLL-Associated Leukemia, Cancer Cell, 2012, 22: 524-535 (Year: 2012).*
International Search Report & Written Opinion for corresponding PCT Application No. PCT/2017/037424 dated Nov. 7, 2017.
Xi Jiang et al, "Eradication of Acute Myeloid Leukemia with FLT3 Llgand-Targeted miR-150 Nanoparticles," Jun. 8, 2016; Downloaded from cancerres.aacrjournals.org on Oct. 23, 2017.
Xi Jiang et al, "Targeted Treatment of FLT3-Overexpressing Acute Myeloid Leukemia with MiR-150 Nanoparticles Guided by Conjugated FLT3 Ligand Peptides," Blood, 2015.

* cited by examiner

*Primary Examiner* — Ekaterina Poliakova-Georgantas
(74) *Attorney, Agent, or Firm* — Dinsmore & Shohl LLP

(57) ABSTRACT

A nanoparticle delivery system designed for sustained delivery of microRNA-150 (miR-150) to FLT3-overexpressing acute myeloid leukemia (AML) cells, the delivery system comprising poly(amidoamine) (PAMAM) dendrimers complexed with miR-150, wherein at least one dendrimer is surface-functionalized with a ligand specific for FLT3 receptor, and methods for treating AML characterized by FLT3-overexpression are provided.

7 Claims, 31 Drawing Sheets
Specification includes a Sequence Listing.

Front   Back   Top

METHODS FOR TREATING SUBJECTS SUFFERING FROM ACUTE MYELOID LEUKEMIA WITH FLT3 LIGAND-TARGETED MIR-150 NANOPARTICLES

PRIORITY CLAIM

This application is a § 371 National Stage Entry of PCT/US2017/037424, filed Jun. 14, 2017, and claims priority to U.S. Provisional application Ser. No. 62/349,707, filed Jun. 14, 2016, the entire disclosure of which is incorporated herein.

GOVERNMENT INTERESTS

This invention was made with government support under Contract No. R01 CA 182528 awarded by the National Cancer Institute of the National Institute of Health. The U.S. government has certain rights in the invention.

BACKGROUND

Acute myeloid leukemia (AML) is one of the most common and fatal forms of hematopoietic malignancies. With standard chemotherapies, only 30-40% of younger (aged <60) and 5-15% of older patients with AML survive more than 5 years. Thus, developing effective therapies is an urgent need in the art.

FMS-like tyrosine kinase 3 (FLT3) encodes a conserved membrane-bound receptor that belongs to the class III receptor tyrosine kinase family. Specific binding of its ligand, FLT3-ligand (FLT3L), leads to the activation of multiple downstream signaling pathways (see, e.g. Kayser S, and Levis M J. *Leuk Lymphoma.* 2014; 55:243-55, incorporated herein). FLT3 is a critical oncogene in hematopoietic malignancies (see also Takahashi S. J, *Hematol Oncol.* 2011; 4:13, and Leung A Y, et al. *Leukemia.* 2013; 27:260-8, incorporated herein).

Internal-tandem duplications (ITDs) and tyrosine kinase domain (TKD) point mutations of FLT3 are found in over 30% of AML cases, id. FLT3-ITD-carrying AMLs are usually associated with poor prognosis (see, e.g. Frohling S, et al. Blood. 2002; 100:4372-80 and Schnittger S, et al. Blood. 2002; 100:59-66, incorporated herein by reference). Previous studies reported that FLT3 was overexpressed in more than 60% of AML cases tested, relative to normal control hematopoietic cells (id). Although a number of FLT3 tyrosine kinase inhibitors (TKIs) have been investigated in clinical trials, the long-term therapeutic effects are disappointing, likely due to secondary mutations in FLT3, up-regulation of FLT3 expression, and/or activation of FLT3 downstream signaling pathways (see, e.g. Leung A Y, et al. Leukemia. 2013; 27:260-8, and Kindler T, et al. Blood. 2010; 116:5089-102). Thus, decreasing the abundance of FLT3 at the RNA and protein levels would be an attractive strategy to treat AMLs with FLT3 overexpression and/or FLT3-ITD/TKD mutations.

MicroRNAs (miRNA) are a class of small, non-coding RNAs that play important roles in post-transcriptional gene regulation. The present inventors recently reported that miR-150 functions as a pivotal tumor-suppressor gatekeeper in MLL-rearranged and other subtypes of AML, through targeting FLT3, MYB, HOXA9 and MEIS1 directly or indirectly (Jiang X, et al. *Cancer Cell.* 2012; 22:524-35, incorporated herein by reference). Jiang et al. further showed that MLL-fusion proteins and MYC/LIN28 up-regulated FLT3 level through inhibiting the maturation of miR-150 (id). These findings strongly suggest a significant clinical potential of restoration of miR-150 expression and function in treating FLT3-overexpressing AML.

However, successful clinical implementation of miRNA-based therapy typically requires a highly specific and efficient delivery system. Viral delivery systems or conventional non-viral systems such as cholesterol conjugates and cationic liposome packaging have often shown severe toxicity and have induced hypersensitive reactions in vivo (see Garzon R, et al. *Nat Rev Drug Discov.* 2010; 9:775-89, incorporated herein by reference). Poly(amidoamine) (PAMAM) dendrimers have been shown to be effective non-viral gene delivery vectors (see Pack D W, et al. *Nat Rev Drug Discov.* 2005; 4:581-93, and Peer D, et al. Nature *Nanotechnology.* 2007; 2:751-60, incorporated herein by reference). Their spherical, chemically well-defined structure, precisely controlled size, multivalency, and capability of forming complexes (dendriplex) with nucleotide oligos render them a potentially suitable platform for miRNA delivery. Clearly, a safe and effective delivery system for an miRNA-based therapy for the treatment of AML is a compelling need in the art.

SUMMARY

Accordingly, the present inventors developed targeted nanoparticles based on FLT3L-guided dendrimers complexed with miR-150 oligos, which exhibited high selectivity and efficiency in targeting leukemic cells with overexpression of FLT3. Preclinical animal model studies have demonstrated the potent in vivo therapeutic effect of embodiments of the FLT3L-guided miR-150 nanoparticles in treating FLT3-overexpressing AML, alone or in combination with other therapeutic agents.

One embodiment of the present invention is directed to a nanoparticle delivery system designed for sustained delivery of microRNA-150 (miR-150) to FLT3-overexpressing AML cells. The delivery system comprises poly(amidoamine) (PAMAM) dendrimers complexed with miR-150, wherein at least one dendrimer is surface-functionalized with a ligand specific for FLT3 receptor.

Another embodiment is directed to methods for treating a patient suffering from acute myeloid leukemia (AML). The methods comprise: administering an FLT3-guided dendromeric nanoparticle complexed with miR-150 to the patient. Yet another embodiment provides methods of treating patients suffering from acute myeloid leukemia, the methods comprise administering G7-Flt3L-(2'OMe)miR-150 to the patient, and in other embodiments, the methods further comprise co-administering one or more BET inhibitors.

Another embodiment provides a nanoparticle delivery system design for sustained delivery of a microRNA to AML cells characterized by overexpression of a gene. The delivery system comprises poly(amidoamine) (PAMAM) dendrimers complexed with the microRNA, wherein at least one dendrimer is surface-functionalized with a ligand specific for the protein expression product of the gene.

These and other embodiments and aspects will be set forth and further elucidated by reference to the Figures and the Detailed Description, below.

Figures are set forth to summarize data that underpins certain concepts relevant to understanding embodiments of the invention, and for illustrative purposes and should not be construed as limiting the full scope of the invention as defined herein and as readily understood by a person of ordinary skill in the art.

BRIEF DESCRIPTION OF THE FIGURES

FIG. 2(A) G7-NH$_2$ PAMAM dendrimers were first conjugated with the near-infrared dye Cy5.5 using an N-hydroxysuccinimide ester linker sulfo-SMCC. Next, the fluorescently-tagged G7-NH$_2$ (G7-Cy5.5) was conjugated to human recombinant FLT3L (i.e., the soluble FLT3L form with 155 amino acids; ProSpec-Tany Technogene Ltd., East Brunswick, N.J.) at a 1:2 ratio using the heterofunctional linker sulfosuccinimidyl 4-((N-maleimidomethyl) cyclohexane-1-carboxylate) (sulfo-SMCC), resulting in the G7-FLT3L conjugates. FIG. 2(B) MONOMAC-6 cells were treated with Cy5.5-conjugated G7-FLT3L or G7-H2B nanoparticles for 24 hrs at the indicated doses. The proportion of Cy5.5$^+$ cells were detected through flow cytometry analysis. FIG. 2(C) MONOMAC-6 and U937 cells were treated with 50 nM Cy5.5-conjugated G7-FLT3L or G7-H2B nanoparticles for 1 hr. The proportion of Cy5.5$^+$ cells were detected through flow cytometry analysis. FIG. 2(D) MONOMAC-6 cells transfected with MSCV-PIG-miR-150 (miR-150-PIG) or MSCV-PIG (PIG) were treated with 50 nM Cy5.5-conjugated G7-FLT3L or G7-H2B nanoparticles for 1 hr. The proportion of Cy5.5$^+$ cells were detected through flow cytometry analysis. Each experiment was repeated independently for at least three times. Average levels of at least three replicates are shown. FIG. 2(E) Cell viability (left panel) and apoptosis (right panel) of MONOMAC-6 cells treated with PBS (Ctrl), 50 nM G7-FLT3L or G7-H2B nanoparticles for 48 hr. *, P<0.05; **, P<0.01.

FIG. 3(A) G7-FLT3L dendrimers were integrated with miR-150 oligos to form stabilized G7-FLT3L-miR-150 dendriplexes. FIG. 3(B) MONOMAC-6 cells were treated with G7-FLT3L or G7-H2B nanoparticles complexed with miR-150 or miR-150 mutant RNA (i.e., Control/Ctrl) oligos at the indicated doses and shows cell viability or FIG. 3(C) cell apoptosis 48 hrs post treatment. FIG. 3(D) total cell count of G7-FLT3L-treated cells at indicated time points post-drug treatment. FIG. 3(E) total cell count of G7-H2B treated groups. FIG. 3(F) MONOMAC-6 cells were treated with G7-FLT3L or G7-H2B nanoparticles complexed with 2'-OMe-modified miR-150 or miR-150 mutant RNA oligos at the indicated doses, showing total cell numbers of G7-FLT3L-treated and FIG. 3(G) G7-H2B-treated groups at the indicated time points, *, P<0.05; **, P<0.01. FIG. 3(H) MONOMAC-6 cells were treated with 50 nM G7-FLT3L-miR-150 or G7-FLT3L control (Ctrl) nanoparticles for 72 hours, showing determined levels of FLT3, phosphorylated STAT5 (Y694), STAT5, phosphorylated AKT (S473), AKT, phosphorylated ERK (T202/Y204), ERK, PIM and ACTIN by Western blotting.

FIG. 4(A) C57BL/6 wild type mice were treated with 0.5 mg/kg Cy5.5-conjugated G7-Flt3L or G7-NH$_2$, i.v., once. Whole animal images at the indicated time points are shown (D1=day 1, etc.). The white arrows indicate the location of femur bone marrow (BM), FIG. 4(B) Uptake ratio of Cy5.5-conjugated G7-Flt3L or G7-NH$_2$ in mouse BM and spleen (SP) cells. Animals were sacrificed 7 days post treatment, and the Cy5.5$^+$ ratio was determined through flow cytometry analysis. FIG. 4(C) Uptake ratio of Cy5.5-conjugated G7-Flt3L or G7-NH2 in mouse BM and SP c-Kit$^+$ or c-Kit$^-$ cells. Cy5.5$^+$ ratio in c-Kit$^+$ or c-Kit$^-$ cell populations is shown. Each experiment was repeated independently for at least three times. Average levels of at least three replicates are shown. *, P<0.05.

FIG. 5(A) Secondary BMT recipient mice transplanted with primary MLL-AF9 AML cells were treated with nanoparticles (G7-NH$_2$-miR-150mut, G7-NH$_2$-miR-150, G7-Flt3L-miR-150mut or G7-Flt3L-miR-150) or PBS control after the onset of AML. The medium survivals of G7-Flt3L-miR-150 group, the control group and the G7-NH$_2$-miR-150 treated group are 86 days, 54 days, and 63 days, respectively. FIG. 5(B) Synergistic therapeutic effect of G7-Flt3L-miR-150 and JQ1. The same MLL-AF9 AML mouse model was employed. Kaplan-Meier curves are shown. G7-NH$_2$-miR-150-FJQ1 v.s. JQ1 alone: P=0.2062; G7-Flt3L-miR-150 v.s. JQ1 alone: P=0.0051. All the P values were detected by log-rank test. FIG. 5(C) sets forth representative images of Wright-Giemsa stained PB and BM, and hematoxylin and eosin (H&E) stained spleen and liver of the MLL-AF9-secondary leukemic mice treated with PBS control, JQ1 and/or miR-150-formulated nanoparticles. Samples were taken at the endpoints or 200 days post-BM transplantation.

FIG. 6(A) cell viability of BM mononuclear cells from a healthy donor, FIG. 6(B) MONOMAC-6 cells, FIG. 6(C) BM mononuclear cells from AML patients bearing t(11;19), FIG. 6(D) t(6;11), FIG. 6(E) t(4;11), FIG. 6(F) FLT3-ITD, FIG. 6(G) t(4;11)/FLT3-ITD, FIG. 6(H) t(9;11), FIG. 6(I) t(9;11), FIG. 6(J) t(8;21), FIG. 6(K) inv(16), FIG. 6(L) U937 cells; cells were treated with PBS, 50 nM G7-NH$_2$-miR-150mut, G7-NH$_2$-miR-150, G7-Flt3L-miR-150mut or G7-Flt3L-miR-150. Cell viability was tested through MTS assays 48 hrs post treatment; FIG. 6(M) shows relative gene expression level of FLT3 for the above samples. *, P<0.05; **, P<0.01.

FIG. 7(A) $^1$H NMR spectra of G7 PAMAM dendrimers before conjugation with Cy5.5, FIG. 7(B) after conjugation with Cy5.5, FIG. 7(C) and after conjugation with FLT3L, the arrow indicates hydrophobic amino acids (isoleucine, valine, and leucine) in FLT3L, suggesting the successful conjugation of the G7 PAMAM dendrimer and FLT3L, the conjugation of Cy5.5 and FLT3L was confirmed by $^1$H NMR analyses. The peaks in the range of 8.5-7.5 ppm indicate the successful conjugation of Cy5.5 to the dendrimers, yielding approximately 4 Cy5.5 molecules per dendrimer; based on the relative integration of peaks ranging from 0.6-1 ppm due to hydrophobic amino acids (isoleucine, valine, and leucine side chains) an average of approximately 0.5-1 FLT3L molecules were conjugated to each G7 dendrimer; FIG. 7(D) representative flow cytometry data of the uptake of the nanoparticles leukemic cell lines are shown for MONOMAC-6 cells treated with Cy5.5-conjugated G7-FLT3L or G7-H2B nanoparticles for 24 hrs at the indicated doses; FIG. 7(E) for MONOMAC-6 and U937 cells treated with 50 nM Cy5.5-conjugated G7-FLT3L or G7-H2B nanoparticles for 1 hr; and FIG. 7(F) for MONOMAC-6 cells transfected with MSCV-PIG-miR-150 (miR-150-PIG) or MSCV-PIG (PIG) and treated with 50 nM Cy5.5-conjugated G7-FLT3L or G7-H2B nanoparticles for 1 hr. The proportions of Cy5.5$^+$ cells were detected through flow cytometry analysis and are labeled in upper frames.

FIG. 8(A) G7-Cy5.5 PAMAM dendrimers are able to retard the migration of a 23 bp ssDNA (to mimic the structure of miR-150) at N/P (amine-to-phosphate) ratios above 1, indicating the successful conjugation of G7-Cy5.5 to ssDNA at N/P (amine-to-phosphate) ratios as low as 1-2; FIG. 8(B) graph of relative intensity as a function of size and FIG. 8(C) graph of size as a function of molar ratio, taken with (B) shows that dendriplex size is inversely proportional to and dependent on molar mixing ratio between G7-Cy5.5 and ssDNA; although dendrimers inhibit gel migration at lower N/P ratios, a molar mixing ratio of 1.5 G7-Cy5.5-to-ssDNA (N/P 33) was chosen in order to minimize the particle size (<200 nm) for improved circulation abilities; based on the nanoparticle sizes, a molar mixing ratio of 1.5 G7-to-oligonucleotide was used for all following experiments to ensure that the nanoparticle size was below 200 nm for optimal circulation abilities and minimal aggregation; FIG. 8(D) graph of total count as a function of apparent zeta potential, the prepared G7-Cy5.5-ssDNA nanoparticles were 142.2+/−113.1 nm with a surface zeta potential of 34.0 mV.

FIG. 10(A)-FIG. 10 (D) evidence the specific targeting and inhibitory effect of G7-Flt3L-miR-150 nanoparticles to FLT3-overexpressing AML cells in vitro; FIG. 10(A) shows the structural homology of FLT3L and the Flt3L peptide; the soluble FLT3L (134~156 amino acids) is generated by protease cleavage of the extracellular domain from the whole FLT3L protein that is a 235-amino acid type I transmembrane protein; the soluble FLT3L is recognized as the major biological active form of FLT3L (see Graddis T J, et al. J Biol Chem. 1998; 273:17626-33, Savvides S N, et al. Nat Struct Biol. 2000; 7:486-91, Lyman S D, et al. Cell. 1993; 75:1157-67, and Lyman S D, et al. Oncogene. 1995; 10:149-57, the entire disclosures of which are incorporated by this reference). Based on previous structure-function analyses of Flt3L reported in the references, a 74-amino acid peptide that contains the A-C helix domains of murine Flt3L was designed. Those functional domains are highly conserved between humans and mice, id. In order to validate the structural homology of the engineered Flt3L, the peptide structure was predicted using the I-TASSER protein structure server (see Roy A, et al. Nat Protocols. 2010; 5:725-38, Yang J. et al. Nat Meth. 2015; 12:7-8, and Yang J, et al. Nucleic Acids Research, incorporated herein by this reference); Flt3L (green) was overlaid over the native full form of the human FLT3 ligand (blue). A high degree of structural similarity is demonstrated, with all major structural components aligning within the structure. These results suggest that the engineered mouse Flt3L peptide is similar in structure to the natural human FLT3L.

FIG. 11(A) cellular level of miR-150 in BM c-Kit$^+$ cells of mice administrated with single dose of G7-Flt3L-miR-150 or G7-Flt3L nanoparticles. C57BL/6 mice were treated with 0.5 mg/kg G7-Flt3L-miR-150 or G7-Flt3L nanoparticles through tail-vein injection. BM samples were collected at the indicated time points post-drug administration. FIG. 11(B) Primary leukemia BM cells bearing MLL-AF9 were transplanted into sublethally irradiated secondary recipient mice. After the onset of secondary AML, the recipient mice were treated with PBS control, 0.5 mg/kg G7-NH$_2$-miR-150, or G7-Flt3L-miR-150, i.v., every other day, until the PBS-treated control group all died of leukemia. BM cells were harvested at the end points and gene expression levels of miR-150, Flt3, Myb, Hoxa9 and Meis1 are shown. At least 3 animals were included in one group. *, P<0.05; **, P<0.01.

DETAILED DESCRIPTION

Figure 1A:
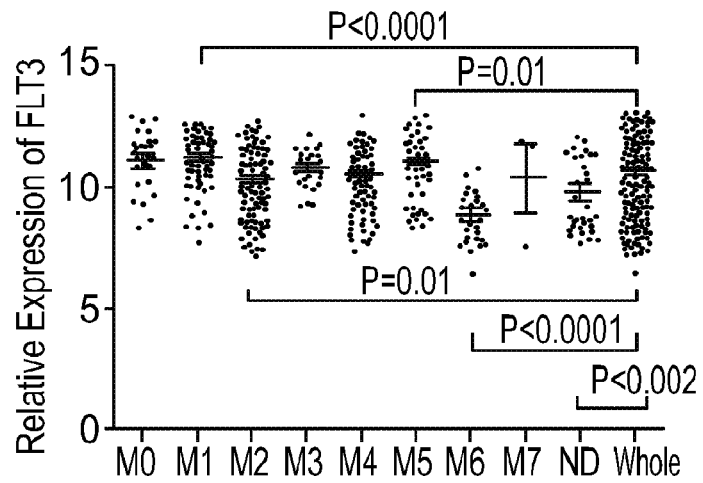
FIG. 1(A)-FIG. 1(C) plots showing that FLT3 is highly expressed and miR-150 is repressed in AML; (A) the expression pattern of FLT3 across FAB cytogenetic subtypes; (B) across subtypes with different molecular mutations; (C) in the GSE37642 AML cohort. For (A) and (B), P-value is shown for the particular AML subtypes in which FLT3 was expressed at a significantly higher or lower level than that in the whole AML set (n=562). In (C), the P-value is shown for comparison between each individual AML subtype (with a particular type of molecular abnormalities) and the whole AML set (left panel), or between AML cases with and without a particular type of molecular abnormalities (right panel). ND=not determined; complex=complex karyotypes; other=other cytogenetic abnormalities; CN=cytogenetically normal; _Mut=with a particular type of molecular mutations; _Neg=without a particular type of molecular mutations. Note: The expression values were log(2) transformed and normalized by RMA as discussed in Irizarry R A et al. *Nucleic Acids Res.* 2003; 31:e15. Over 40% of the AML cases with NPM1 mutations also have FLT3-ITD.

Acute myeloid leukemia (AML) is a common and fatal form of hematopoietic malignancy. Overexpression and/or mutations of FLT3 have been shown to occur in the majority cases of AML. Embodiments of the invention provide FLT3L-guided nanoparticles complexed with miR-150, a potent tumor suppressing miRNA, which exhibit a high specificity and efficiency in targeting FLT3-overexpressing AML. Animal model studies confirm the feasibility and effectiveness of the delivery system and provide new therapeutic strategies for clinical applications in treating FLT3-overexpressing AMLs, the majority of AML cases that are resistant to presently available standard chemotherapies.

FLT3 is particularly highly expressed in some subtypes of AML such as AML with t(11q23)/MLL-rearrangements or FLT3-ITD. Such AML subtypes are known to be associated with unfavorable prognosis. To treat FLT3-overexpressing AML, a novel targeted therapeutic strategy using FLT3L-guided miR-150-based nanoparticles to treat FLT3-overexpressing AML with high efficacy and minimal side effects is disclosed. The FLT3L-guided miR-150 nanoparticles selectively and efficiently target FLT3-overexpressing AML cells, and significantly inhibit viability/growth and promote apoptosis of the AML cells. Employing animal models, the FLT3L-guided miR-150 nanoparticles are shown to concentrate in bone marrow and significantly inhibit progression of FLT3-overexpressing AML in vivo, while exhibiting no obvious side effects on normal hematopoiesis.

Analysis of a large cohort of AML patients (n=562), was used to provide a more precise understanding of the patterns of FLT3 expression in AML. While FLT3 is likely overexpressed in the vast majority of primary AML cases, it is particularly highly expressed in a set of AML subtypes including FAB M1/M2/M5 AML and AML with t(11q23)/MLL-rearrangements, or FLT3-ITD and/or NPM1 mutations. As AMLs with t(11q23) or FLT3-TTD, accounting for over 40% of total AML cases, are often associated with poor outcome, it is urgent to develop targeted therapeutic strategies to treat such FLT3-overexpressing, poor-prognosis AMLs.

In order to selectively target FLT3-overexpressing AMLs, the present inventors developed novel, FLT3L-guided, dendrimer-based nanoparticles for the targeted delivery of miR-150 oligos to FLT3-overexpressing AML cells. The inventive nanoparticle delivery system confers the following advantages: (i) growth and proliferation of FLT3-overexpressing AML cells is inhibited by restoration of the expression and function of a pivotal tumor-suppressor miRNA (i.e., miR-150) that post-transcriptionally inhibits the expression of FLT3 (at the RNA level). The direct repression of FLT3 expression avoids the potential rebound of FLT3 expression induced by other treatments, e.g., FLT3 TKI treatment; (ii) FLT3L is employed as the guiding molecule to specifically deliver miR-150 oligos to FLT3-overexpressing AML cells and thus achieves selective targeting; and (iii) G7 PAMAM dendrimers are utilized as the carriers for miRNA delivery. G7 PAMAM dendrimers have a large surface area, flexible architecture, and multivalent binding capability that facilitate tight cell surface binding. The high density of positive charges on their surface also facilitates interaction with the cell membrane and subsequent cellular uptake. The inventive G7-FLT3L-miR-150 nanoparticles confer unique advantages and exhibit specific targeting and potent anti-leukemia effects on FLT3-overexpressing AML cells both in vitro and in vivo.

One embodiment is directed to a nanoparticle delivery system designed for sustained delivery of microRNA-150 (miR-150) to FLT3-overexpressing AML cells. The delivery system comprises poly(amidoamine) (PAMAM) dendrimers complexed with miR-150, wherein at least one dendrimer is surface-functionalized with a ligand specific for FLT3 receptor. PAMAM dendrimers have what is commonly referred to in the art as "molecular Velcro" surfaces, making them desirable for use in targeted delivery systems where it is possible to functionalize suitably to guide to the target and where it is possible to integrate/complex a payload into the dendrimeric complex. The PAMAM dendrimers are hyper-branched nanoscale polymers with a high degree of molecular uniformity and therefore shape and size. The polymer consists of an ethylenediaime core and a repetitive branching amido-amine branching structure with a primary amine, and therefor highly reactive, terminal surface. The dendrimers are grown in an interative manufacturing process with each step referred to as yielding a "generation" of dendrimer. The larger the dendrimer generation (G1, G2 . . . G7 . . . G9 . . . etc.), the larger the diameter of the molecule, with each successive generation having double the molecular weight and twice the number of reactive surface sites as the preceding generation. Beginning with G4, the dendrimer forms a roughly spherical shape. According to specific embodiments, the PAMAM dendrimers comprise between generation-1 (G4) and G8 dendrimers (G4, G5, G6 G7 and G8, or combinations thereof). According to very specific embodiments, the PAMAM dendrimers comprise one to four, or more specifically 3, G7 dendrimers.

According to other specific embodiments, the ligand specific for FLT3 receptor comprises a natural or synthetic FLT3L peptide, and in more specific embodiments, the ligand specific for FLT3 receptor comprises a synthetic FLT3L peptide having at least 50%, 60%, 70%, 80% or 90% sequence homology to SEQ ID NO: 2. Functionally, the suitable synthetic FLT3L peptide must retain binding affinity for the FLT3 receptor. According to very specific embodiments, the synthetic FLT3L peptide is Flt3L peptide, although it will be readily perceived by a person of ordinary skill in the art that the surface peptide may be any FLT3L derivative that retains binding affinity for the target receptor.

In some embodiments, the miR-150 is modified for stability. miR-150 is also known in the literature as MIRN150, mir-150, and MIR-150 (official name). microRNAs are short (20-24 nt) non-coding RNAs that are involved in post-transcriptional regulation of gene expression in multicellular organisms by affecting both the stability and translation of mRNAs. A mature miRNA is incorporated into a RNA-induced silencing complex (RISC), which recognizes target mRNAs through imperfect base pairing with the miRNA and most commonly results in translational inhibition or destabilization of the target mRNA.

In preliminary experiments, the desired efficacy was undesirably transient. Therefore the miR-150 was modified via 2'-O methylation, which resulted in a sustained effect. In very specific embodiments, the nanoparticle delivery system comprises G7-Flt3L-(2' OMe)miR-150.

The data set forth herein demonstrates that restoration of miR-150 expression/function holds a great therapeutic potential in treating AML characterized by FLT3 overexpression. The 2'-OMe-modified miR-150 oligos delivered by targeted nanoparticles show a high stability and exhibit long-term and potent inhibitory effects on the proliferation and growth of FLT3-overexpressing AML cells in vitro and on the progression of the leukemia in vivo. The present inventors are the first to show that an engineered ligand protein/peptide can be used as a guiding molecule when conjugated to a G7 PAMAM-miRNA dendriplex for specific targeting of leukemic cells with an abnormally high level of the corresponding cell surface receptors. Both the entire soluble FLT3L proteins (with 155 amino acids) and synthetic Flt3L peptides (exemplified by a peptide with 74 amino acids, but clearly encompassing any synthetic peptide capable of ligand-bonding to the FLT3L receptor protein) work very well as the guiding molecules for specific targeting of FLT3-overexpressing AML cells. Compared to nanoparticles conjugated with control proteins, FLT3L-conjugated nanoparticles showed more than 4 times higher specificity and efficiency in targeting and uptake by FLT3-overexpressing AML cells. Compared to control nanoparticles, Flt3L-conjugated nanoparticles tend to concentrate in the BM rather than distribute pervasively throughout the abdomen following injection, and their accumulation is significantly enhanced in c-Kit$^+$ leukemic progenitor cells in both BM and spleen tissues.

Another embodiment is directed to methods of treating patients suffering from acute myeloid leukemia (AML). Broadly, the method comprises: administering an FLT3-guided dendromeric nanoparticle complexed with miR-150 to the patient. The AML is characterized by overexpression of FLT3. Other analogous delivery systems may be designed, based on the strategic template disclosed herein, to target any AML cell characterized by an over-expression of a gene (and/or the protein expression product). The guiding surface functionality comprises a ligand with binding affinity for the protein expression product.

According to specific embodiments of the novel methods, FLT3-guided dendromeric nanoparticle comprises a PAMAM dendromir that is surface-functionalized with a ligand specific for FLT3 receptor. The surface-functionalized ligand comprises FLT3L or a natural or synthetic derivative peptide thereof. In very specific embodiments, the ligand specific for FLT3 receptor comprises a synthetic FLT3L peptide having at least 90% sequence homology to SEQ ID NO: 2. In more specific embodiments, the ligand specific for FLT3 receptor comprises Flt2L peptide. In some specific embodiments, the PAMAM dendromir comprises a G2, G3, G4, G5, G6, G7, or G8-dendromir. In more specific embodiments, the PAMAM dendromir comprises a G4, G5, G6 or G7-dendromir, or combinations thereof. In very specific embodiments, the PAMAM dendromir comprises a G7 dendromir.

Stability of the miR-150 (desired time of action) may be manipulated by modifications. For sustained effect, the miR-150 comprises a stability modification, or example, the miR-150 may be 2'O-methylated. For example, a methyl group may be added to the 2'-position of the ribose on the terminal nucleotide. In very specific embodiments, the complexed nanoparticle comprises G7-Flt3L-(2'OMe)miR-150.

According to some embodiments, administering comprises systemic administration, for example, intravenous administration. As will be readily understood by a clinician of skill in the art, what constitutes a therapeutically effective dose will be highly dependent on the age/gender/body mass index, and other specific physiological attributes and health status of the patient, and especially in the context of treatment of leukemia, due to the need for therapeutic precision, should be determined on a patient-by-patient basis. Targeted delivery of microRNA, where delivery does not substantially occur absent binding of the functionalized dendromeric complex to the target cell, minimizes the likelihood both of undesirable effects in non-target areas and of overdosing a target area.

One embodiment contemplates a method of treating patients suffering from AML comprising administering an embodiment of the microRNA-150 nanoparticle delivery system together with at least one bromodomain (BD) and extra terminal motif protein inhibitor (BET inhibitor). The latter actives have established efficacy in the treatment of particular AML. Surprisingly, a synergistic effect was discovered upon co-administration of the miR-150 with a BET inhibitor. In specific embodiments, the selected BET inhibitor targets both BD1 and BD2. In more specific embodiments, the BET inhibitor is selected from the group consisting of JQ1, I-BET 151, I-BET 762, OTX-015, TEN-010, CPI-201, CPI-0610, and combinations thereof. According to very specific embodiments, the BET inhibitor comprises JQ1. The BET inhibitor may be administered in a single composition, in different compositions, either simultaneously or prior to or subsequent to administration of the miR-150 nanoparticle delivery system.

According to other embodiments, PAMAM dendrimer FLT3-guided miR-150 nanoparticles or more specific embodiments of the nanoparticle delivery system may be combined with FLT3 TKIs to treat AML carrying FLT3-ITD or TKD mutations, which will inhibit both the expression and enzymatic activity of FLT3 and thereby will likely result in a potent long-term therapeutic effect, as FLT3-TKI-induced rebound of FLT3 level and secondary mutations in FLT3 TKD can be inhibited by G7-Flt3L-miR-150 nanoparticles at the transcript level.

By extension, it should be possible to design analogous nanoparticle systems for targeting other AMLs (e.g., AMLs with abnormally high level of c-KIT) by changing the targeting molecule from FLT3L to other molecules (e.g., c-KIT ligand). G7 PAMAM dendrimer-based conjugates are demonstrated herein to be ideal carriers for miRNA delivery to treat AML. Such carriers do not trigger any noticeable side effects on normal hematopoiesis in vivo. The animal studies reported herein demonstrated that the G7-Flt3L-miR-150 nanoparticles were able to substantially inhibit leukemia progression and prolong survival of the treated mice that carried FLT3-overexpressing AML, while exhibiting no obvious side effects on normal hematopoietic system. One broad embodiment is directed to a nanoparticle delivery system designed for sustained delivery of microRNA to AML cells characterized by overexpression of one or more genes or corresponding protein expression products, the delivery system comprising poly(amidoamine) (PAMAM) dendrimers complexed with the microRNA, wherein at least one dendrimer is surface-functionalized with ligand specific for the one or more protein expression products.

The following examples are set forth to illustrate particular aspects and embodiments of the invention and should not be construed as limiting the full scope of the invention as defined by the appended claims.

EXAMPLES

The following apply generally to the Examples set forth below:
Microarrays and Data Analysis of GSE37642 Cohort The patient samples (n=562) samples were analyzed by use of Affymetrix Human Genome U133Plus2.0 GeneChips or Affymetrix Human Genome U133A and B (U133A+B) GeneChips. The RMA5 method (Irizarry R A, et al. *Nucleic*

Acids Res. 2003; 31) was used for data normalization and the expression values were log(2) transformed. Microarrays and data analyses were conducted as described previously (Li Z, et al. *J Clin Oncol*. 2013; 31:1172-81, and Herold T, et al. *Blood.* 2014; 124:1304-11, incorporated herein by reference). The GEO ID of the entire data set is GSE37642.

Nano-Materials

G7 PAMAM dendrimer were obtained from Sigma-Aldrich (St. Louis, Mo.). N-hydroxysuccinimide ester of cyanine5.5 (NHS-Cy5.5) was purchased from Lumiprobe Corporation (Hallandale Beach, Fla.). Sulfo-SMCC was obtained from Thermo Fisher Scientific (Rockford, Ill.). miR-150 and miR-150 mutant RNA oligos (with or without 2'-OMc modification) were purchased from Exiqon Inc. (Woburn, Mass.). The RNA sequences are:

miR-150:
(SEQ ID NO: 2)
5'-UCU CCC AAC CCU UGU ACC AGU G-3';

miR-150 mutant:
(SEQ ID NO: 3)
5'-UUA UUU UAC CCU UGU ACC AGU G-3'.

Human recombinant FLT3L proteins were ordered from ProSpec-Tany Technogene Ltd. (East Brunswick, N.J.), which contain 155 amino acids of the extracellular domain of FLT3L (i.e., the soluble FLT3L form). The synthetic Flt3L peptide containing 74 amino acids with the sequence of SSNFKVKFRELTDHLLKDYPVTVAVNLQDEKHCKA-LWSLFLAQRWIEQLKTVAGSK MQTLLEDVNTEIHFVTSC (SEQ ID NO: 1) was purchased from Pierce Biotechnology, Inc. (Rockford, Ill.).

Preparation of G7-FLT3L or G7-Flt3L Dendrimers

G7 PAMAM dendrimers obtained from Sigma-Aldrich were purified and fluorescently labelled using an N-hydroxysuccinimide ester of cyanine5.5 (NHS-Cy5.5) (Lumiprobe Corporation, Hallandale Beach, Fla.), as has been previously reported (Modi D A, et al. *Nanoscale*. 2014; 6:2812-20, incorporated herein by reference). Human soluble FLT3 protein- or mouse Flt3L peptide-conjugated G7 dendrimers were prepared as previously described, also in Modi et al.

AML Samples and Cell Lines

Patient samples were obtained at the time of diagnosis with informed consent at the University of Chicago Hospital (UCH) or other collaborative hospitals, and were approved by the institutional review board of the institutes/hospitals. All patients were treated according to the protocols of the corresponding institutes/hospitals. All the AML cell lines used herein were originally obtained from ATCC (Manassas, Va.) and maintained at the Chen laboratory.

RNA Extraction and Quantitative RT-PCR

Total RNA was extracted with the miRNeasy extraction kit (Qiagen, Valencia, Calif.) and was used as template for quantitative RT-PCR (qPCR) analysis as described previously (Jiang X, et al. *Cancer Cell*. 2012; 22:524-35, incorporated herein by reference).

Cell Culture and Drug Treatment

MONOMAC-6 and U937 cells were cultured as described previously (Li Z, et al. *Nat Commun*. 2012; 2:688, incorporated herein by reference). Continued testing to authenticate these cell lines was done using qPCR and Western blot to validate the existence or absence of MLL-AF9 when the cell lines were used in this project. Both cell lines were tested for mycoplasma contamination yearly using a PCR Mycoplasma Test Kit (PromoKine) and were proven to be mycoplasma negative. BM mononuclear cells from healthy donors or AML patients were grown in RPMI medium 1640 containing 10% FBS, 1% HEPES and 1% penicillin-streptomycin, supplemented with 10 ng/mL SCF, TPO, Flt3L, IL-3 and IL-6. Cells were treated with PBS, G7-$NH_2$-miR-150mut, G7-$NH_2$-miR-150, G7-Flt3L-miR-150mut or G7-Flt3L-miR-150 at the indicated doses.

Cell Apoptosis, Viability and Proliferation Assays

These assays were conducted as described previously (Li Z, et al. *Nat Commun*. 2012; 2:688) with ApoLive-Glo Multiplex Assay Kit, or CellTiter 96 $AQ_{ueous}$ Non-Radioactive Cell Proliferation Assay Kit (Promega).

Mouse Bone Marrow Transplantation (BMT) Followed with Drug Treatment

Secondary mouse BMT was carried out as described previously (Jiang X, et al. *Cancer Cell*. 2012; 22:524-35). After the onset of leukemia (when mice had an engraftment (CD45.1) of over 20% and/or white blood cell counts higher than $4 \times 10^9$/L, usually 10 days post transplantation), the recipient mice were injected with PBS control, 0.5 mg/kg G7-$NH_2$-miR-150mut, G7-$NH_2$-miR-150, G7-Flt3L-miR-150mut or G7-Flt3L-miR-150, i.v., every other day, until the PBS-treated control group all died of leukemia. For the JQ1 and nanoparticle combination treatment experiment, after the onset of AML, the recipient mice were treated with PBS control, or 50 mg/kg JQ1, i.p., alone, or together with 0.5 mg/kg G7-$NH_2$-miR-150, or G7-Flt3L-miR-150, i.v., every other day, until the PBS-treated control group all died of leukemia.

The Maintenance, Monitoring, and End-Point Treatment of Mice

All laboratory mice were maintained and monitored as previously described (Jiang X, et al. *Cancer Cell*. 2012; 22:524-35).

Statistical Software and Statistical Analyses

The microarray data analysis was conducted by use of Partek Genomics Suite (Partek Inc, St. Louis, Mich.). The t-test, Kaplan-Meier method, and log-rank test, etc. were performed with WinSTAT (R. Fitch Software), GraphPad Prism version 5.00 (GraphPad Software, San Diego, Calif.), and/or Partek Genomics Suite (Partek Inc). The P-values less than 0.05 were considered as statistically significant.

Example 1

Overexpression of FLT3 in AMLs

Figure 1B:
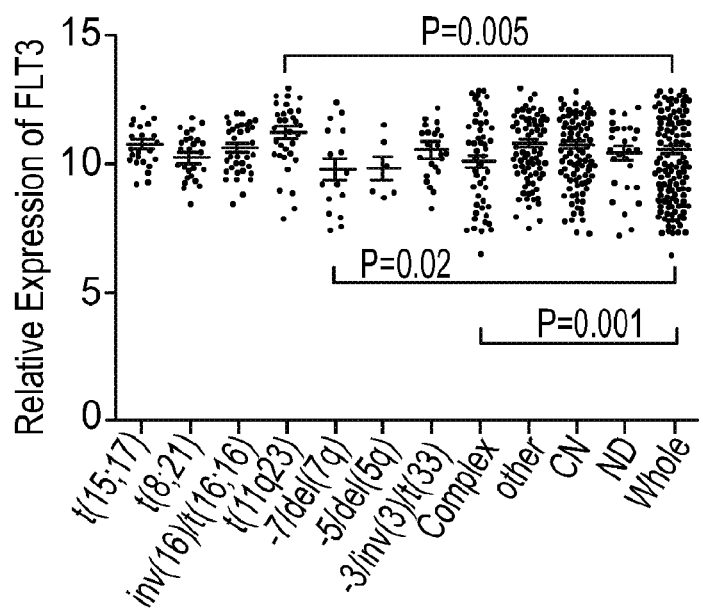
Figure 1C:
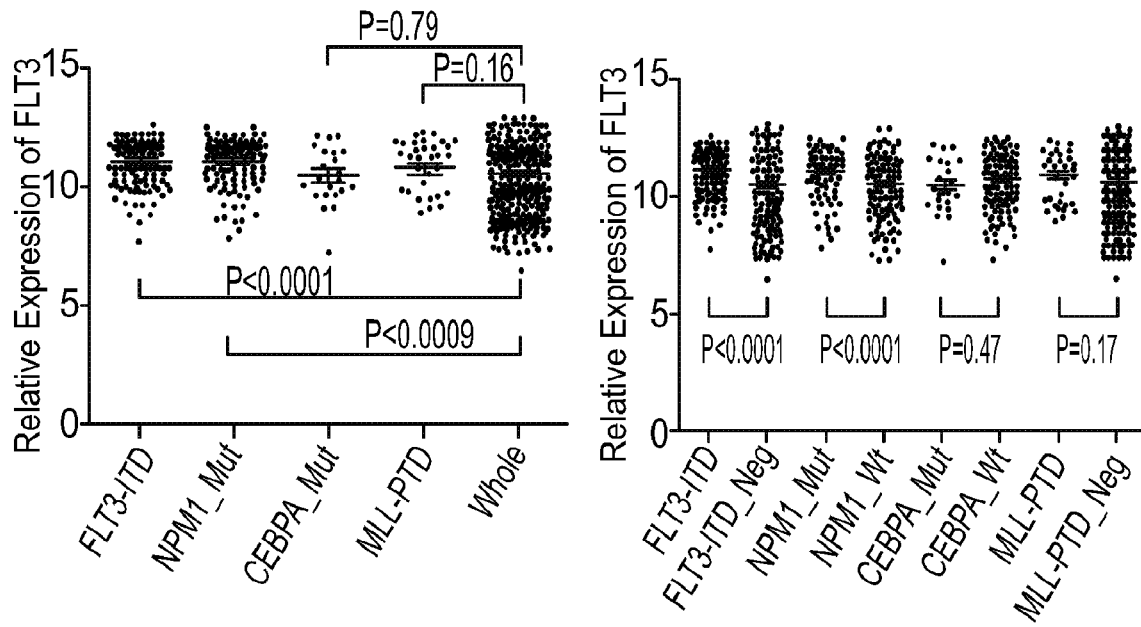
Figure 1D:
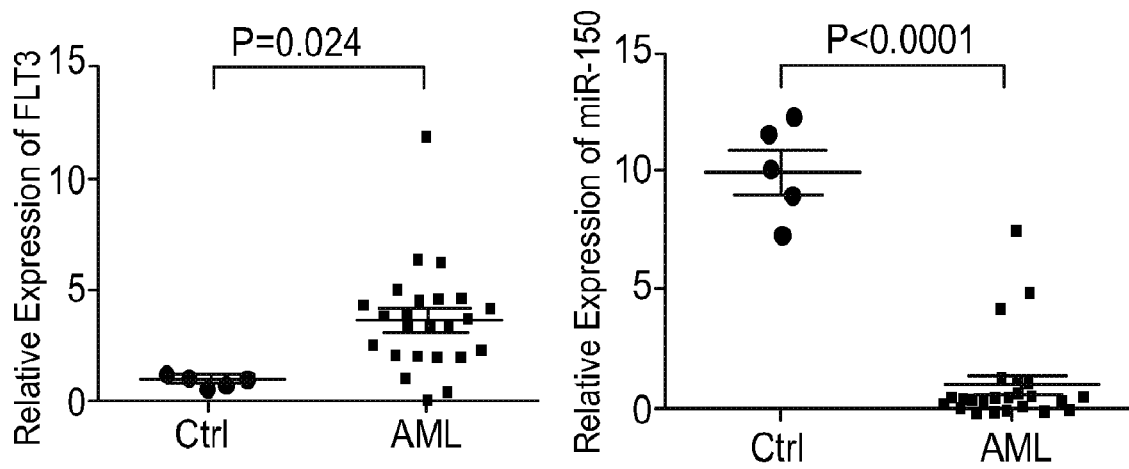
FIG. 1(D) a qPCR analysis of expression of both FLT3 and miR-150 in 23 human primary AML mononuclear (MNC) samples including 3 t(4;11), 1 t(6;11), 9 t(9;11), 1 t(11;19), 3 t(8;21), 1 t(15;17), 3 inv(16), 1 FLT3-ITD, and 1 t(4;11)/FLT3-ITD, along with 5 normal BM cell controls (Ctrl; including 3 MNC and 2 CD34$^+$ samples). The P-values were calculated by two-tailed t-test.

Previous studies, based on relatively small numbers of AML patients (merely 200 patients or fewer), have shown that FLT3 is overexpressed in the majority cases of primary AML relative to normal control cells, whereas controversial observations have been reported regarding the association of FLT3 overexpression with specific AML subtypes (Wang Y G, et al. *Zhonghua xue ye xue za zhi*. 2008; 29:741-5, and Riccioni R, et al. *Br J Haematol*. 2011; 153:33-42, incorporated herein by reference). Here FLT3 expression across various AML subtypes was analyzed in a microarray-based gene-expression dataset of 562 AML patients (GSE37642) (Table 1). Amongst various FAB subtypes, the expression level of FLT3 in the FAB M1, M2 and M5 AML subgroups was significantly higher than its average level in the entire set of AML samples (FIG. 1A). Amongst AML subtypes with different cytogenetic abnormalities, the average expression level of FLT3 in AML with t(11q23)/MLL-rearrangements was significantly higher than that in the whole set of AML samples, whereas the opposite was true in AML with −7/del(7q) or complex karyotypes (FIG. 1B). In AML with distinct molecular abnormalities, the average expression level of FLT3 in AML with FLT3-ITD and/or NPM1 mutations was significantly higher than that in the whole set of AML or AML without the relevant mutations (FIG. 1C). qPCR analysis of expression of both FLT3 and miR-150 was conducted in 23 human primary AML samples and 5 normal control samples. As shown in FIG. 1D, FLT3 is expressed at a higher level in 21 (91%) out of the 23 AML samples, whereas miR-150 is expressed at a lower level in all the 23 AML samples than its average level in the 5 normal controls.

TABLE 1

Clinical and molecular characteristics of the AML patients in GSE37642 cohort

| Characteristic | Entire set (n = 548)[a] |
|---|---|
| Sex - no. (%) | |
| Male | 274 (50) |
| Female | 274 (50) |
| Age - year | |
| Median | 57 |
| Range | 18-85 |
| Overall Survival - year | |
| Median | 1 |
| Range | 0-12 |
| White-cell count - $1 \times 10^{-3}/mm^3$ | |
| Median | 20 |
| Range | 01-666 |
| BM Blast cell count - % | |
| Median | 80 |
| Range | 10-100 |
| Platelet count - $1 \times 10^{-3}/mm^3$ | |
| Median | 50 |
| Range | 0.1-1,760 |
| FAB type - no. (%) | |
| M0 | 22 (4) |
| M1 | 113 (21) |
| M2 | 163 (30) |
| M3 | 26 (5) |
| M4 | 121 (22) |
| M5 | 66 (12) |
| M6 | 22 (4) |
| M7 | 3 (0.5) |
| Not determined | 12 (2) |
| Cytogenetic abnormalities - no. (%) | |
| t(15; 17) | 21 (4) |
| t(8; 21) | 30 (5) |
| inv(16)/t(16; 16) | 38 (7) |
| t(11q23) | 37 (7) |
| t(9; 11) | 19 (3) |
| t(11q23) not including t(9; 11) | 18 (3) |
| −7/del(7q) | 16 (3) |
| −5/del(5q) | 5 (1) |
| −3/inv(3)/t(3; 3) | 14 (3) |
| Complex karyotype | 74 (14) |
| Other abnormal karyotype | 87 (16) |
| Cytogenetic normal | 197 (36) |
| Not determined | 29 (5) |
| Molecular abnormalities - no. (%) | |
| FLT3-ITD | 130 (24) |
| N- or K-RAS | NA |
| NPM1 | 113 (21) |
| CEBPA | 21 (4) |
| MLL-PTD | 33 (6) |

Example 2

Figure 2A:
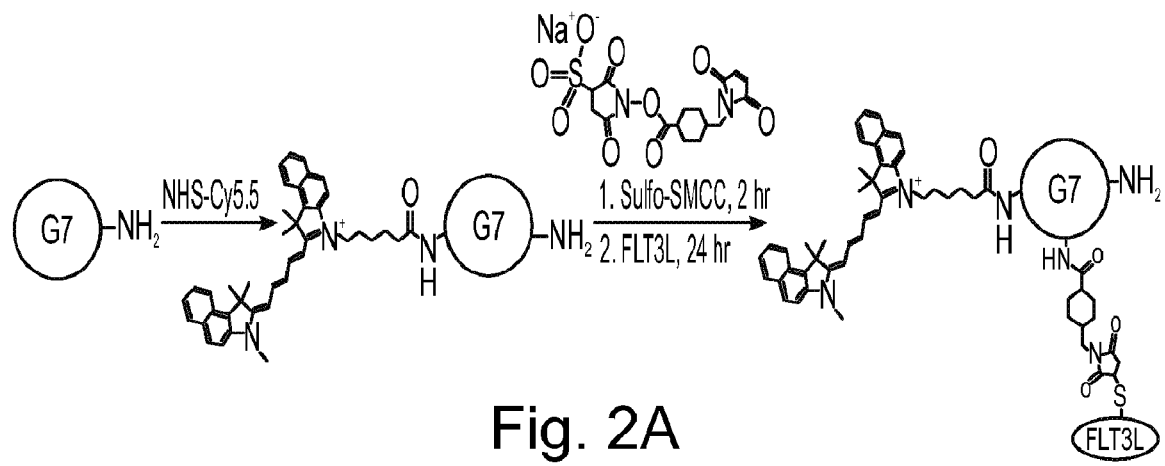
FIG. 2(A)-FIG. 2(E) shows development of G7-FLT3L dendrimers and their selective targeting to FLT3-overexpressing AML cells.
Figure 7A:
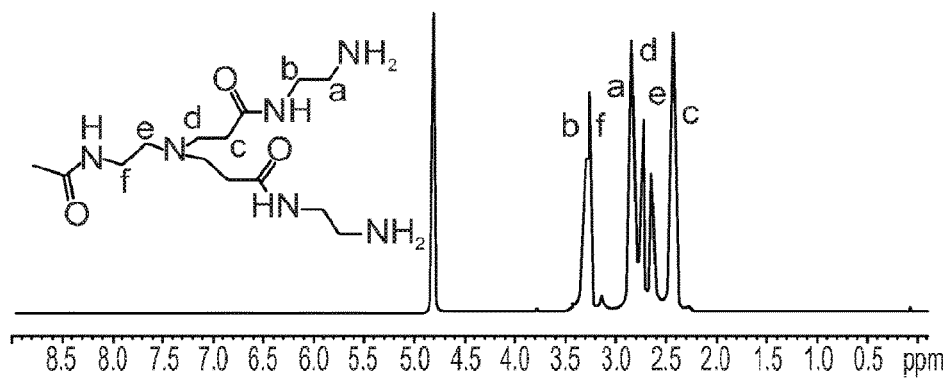
FIG. 7(A)-FIG. 7(F) shows construction of G7-FLT3L dendrimers and their uptake ratio in AML cells.
Figure 7B:
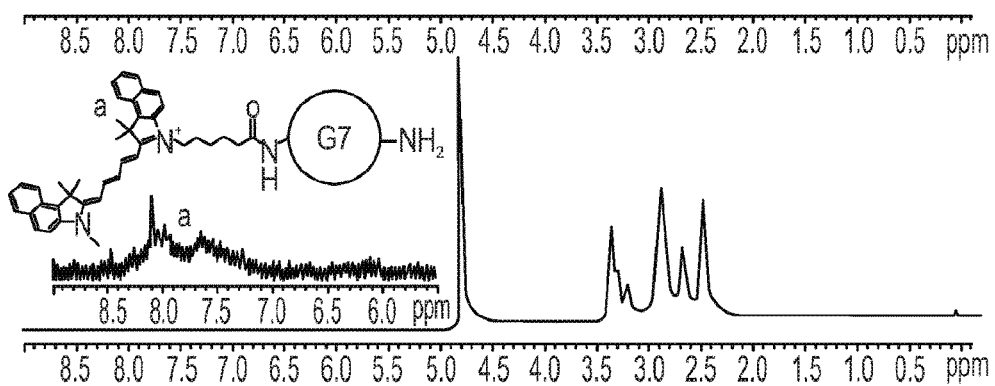
Figure 7C:
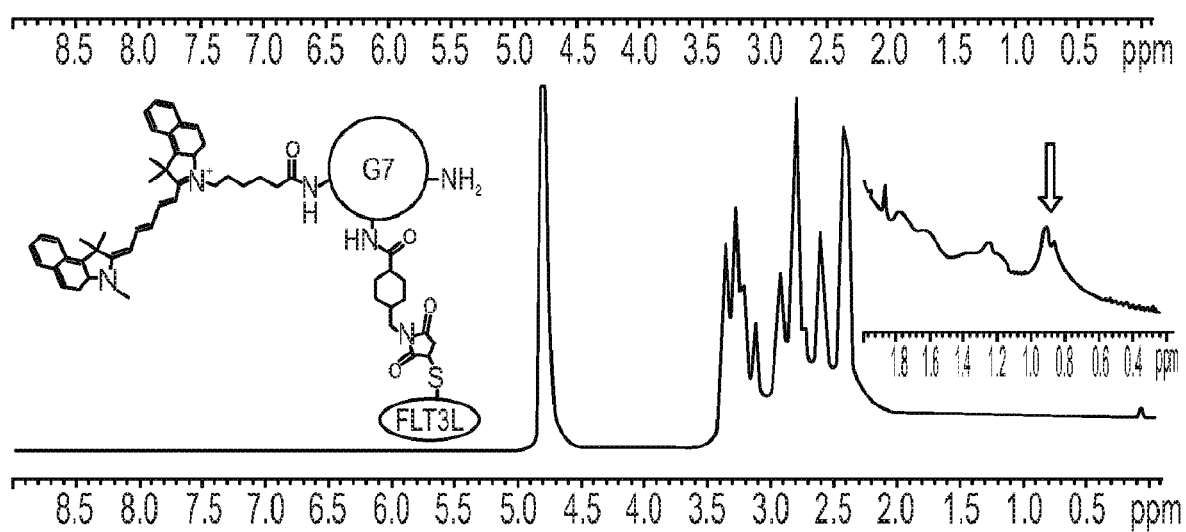

Development of FLT3L-Conjugated Generation 7 (G7) PAMAM (G7-FLT3L) Dendrimers for Selective Delivery In order to selectively deliver miR-150 oligos to FLT3-overexpressing AML cells, Poly(amidoamine) (PAMAM) dendrimers (Hong S, et al. *Bioconjugate Chemistry*. 2006; 17:728-34, Hong S, et al. *Bioconjugate Chemistry*. 2009; 20:1503-13, and Sunoqrot S, et al. *J Control Release*. 2014; 191:115-22, incorporated herein by reference) were selected as the basis of the nanoparticle carriers, and conjugated with the near-infrared dye Cyanine 5.5 (Cy5.5) for monitoring the dynamic distributions of the nanoparticles, and FLT3 ligand (FLT3L) proteins for specific targeting FLT3 on the cell surface. H2B, a nuclear histone protein with similar molecular weight as FLT3L, was conjugated as a negative control (FIG. 2A; FIG. 7A-7C). Whether G7-FLT3L dendrimers can efficiently and selectively target AML cells with FLT3 overexpression was then investigated. After 24 hours' treatment of the nanoparticles, the uptake ratios of the G7-FLT3L dendrimers were significantly higher than the G7-H2B control nanoparticles in MONOMAC-6 cells, an AML cell line carrying the t(9;11)/MLL-AF9 (i.e., the most common form of MLL-rearranged AML(Krivtsov A V, et al. *Nat Rev Cancer*. 2007; 7:823-33 and Slany R K. *Haematologica*. 2009; 94:984-93, both incorporated by reference)).

Figure 2B:
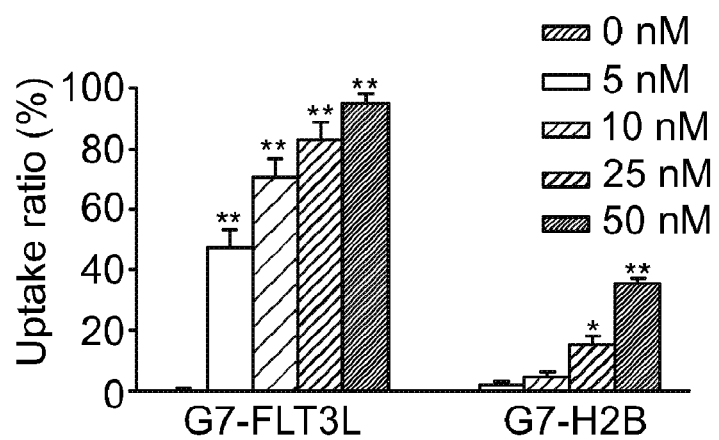
Figure 2C:
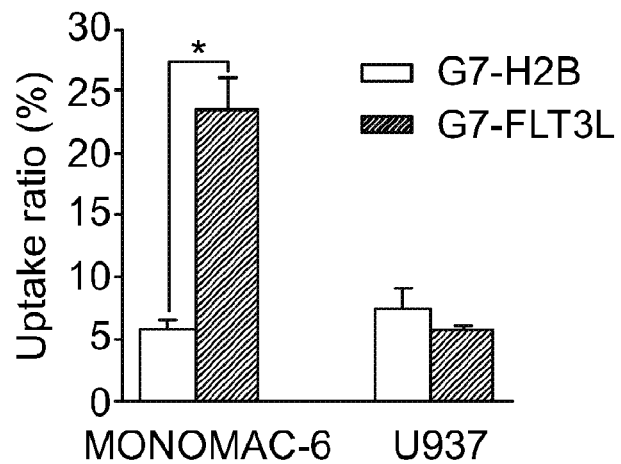
Figure 7D:
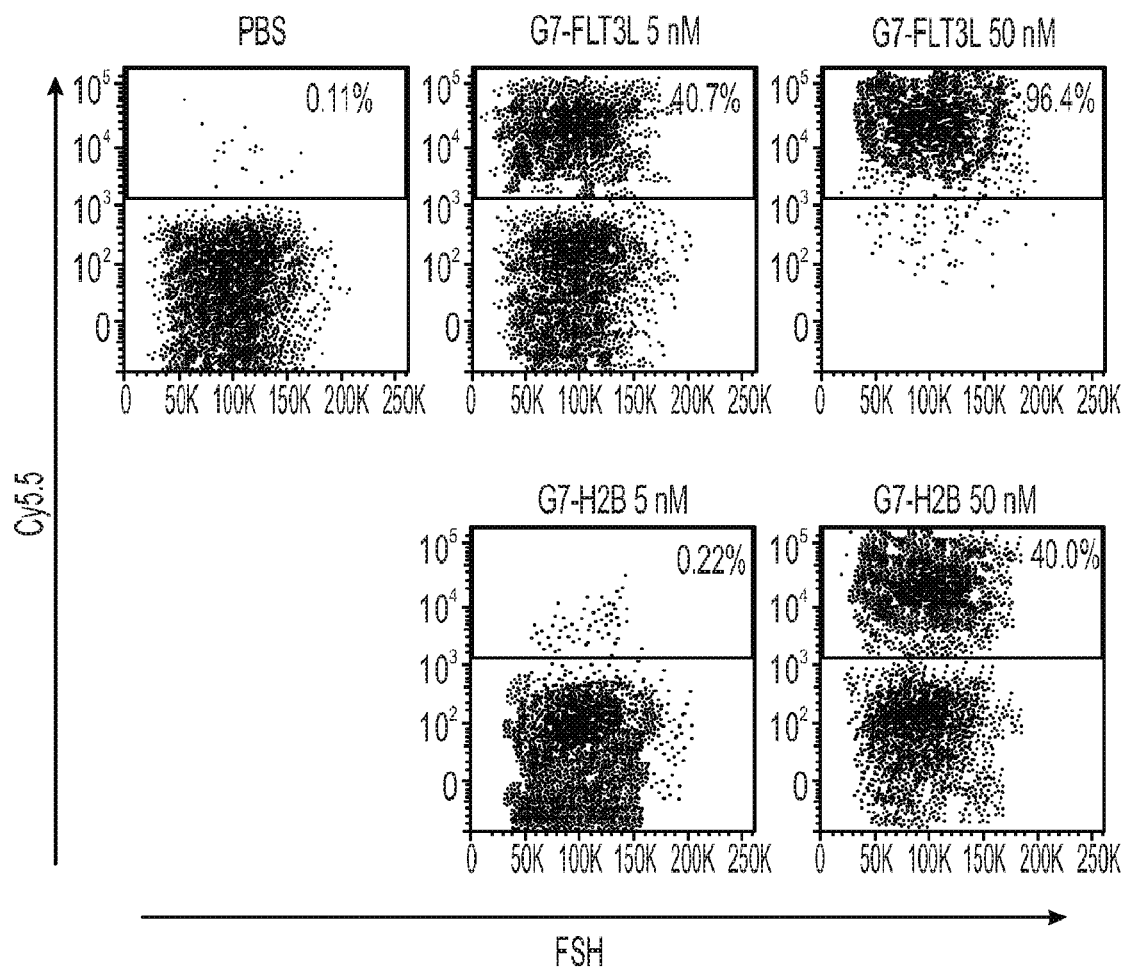
Figure 7E:
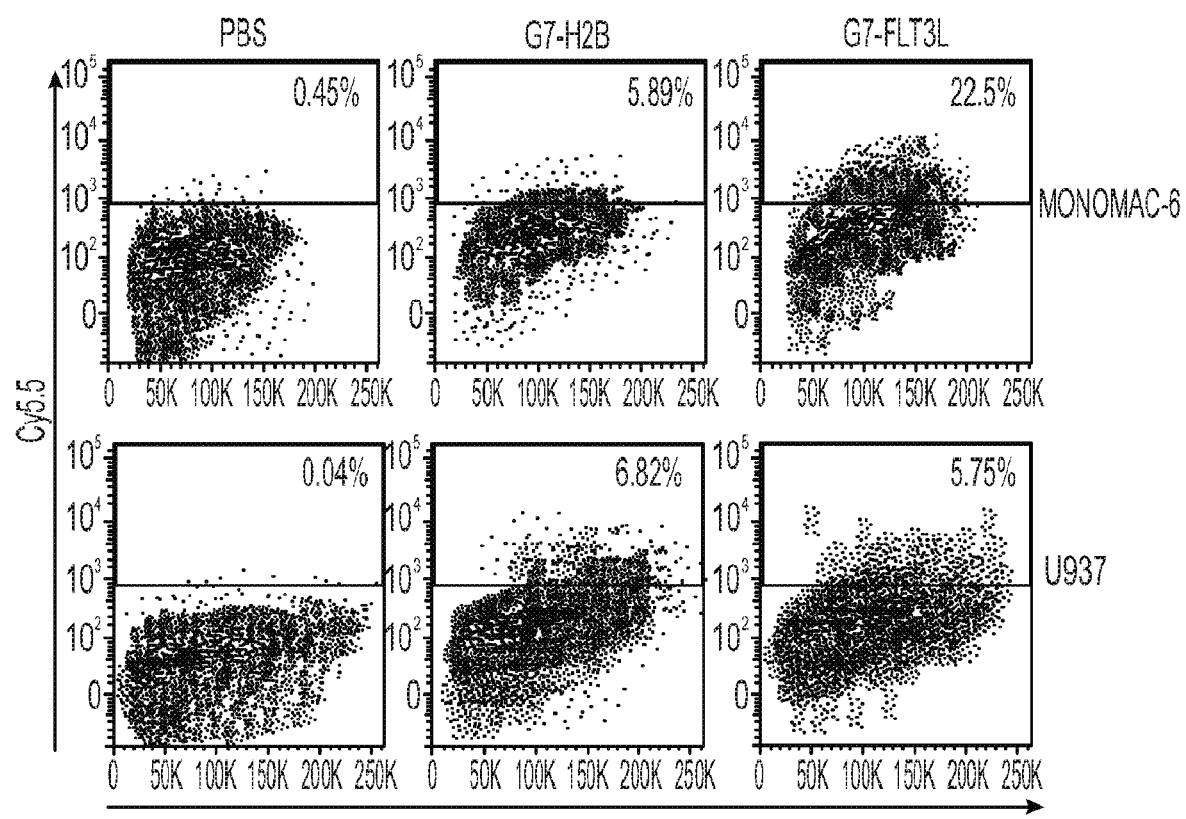

The nanoparticles were taken up in a dose dependent manner (FIG. 2B; FIG. 7D). In addition, the cellular uptake of G7-FLT3L nanoparticles by FLT3-overexpressing AML cells is rapid. Just one hour post the treatment of the nanoparticles, the uptake ratio of G7-FLT3L dendrimers was already 23.6%, significantly higher than that (5.9%) of G7-H2B dendrimers (FIG. 2C; FIG. 7E). In contrast, the uptake ratios between G7-FLT3L and G7-H2B dendrimers showed no significant difference in U937 cells (a cell line with very low levels of FLT3 (16, 41)) (FIG. 2C; FIG. 7E).

Figure 2D:
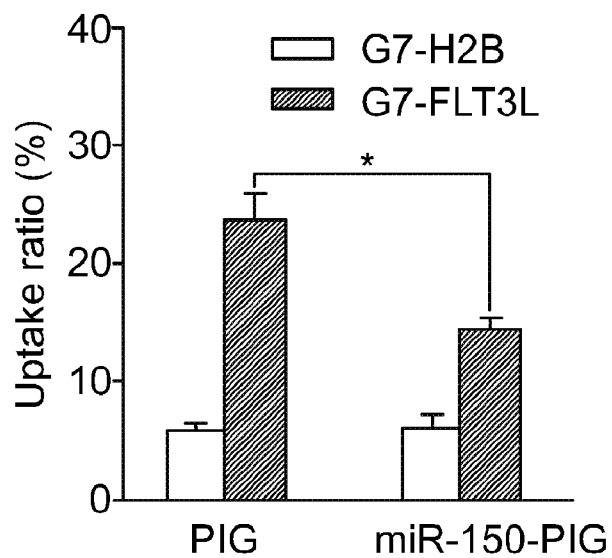
Figure 2E:
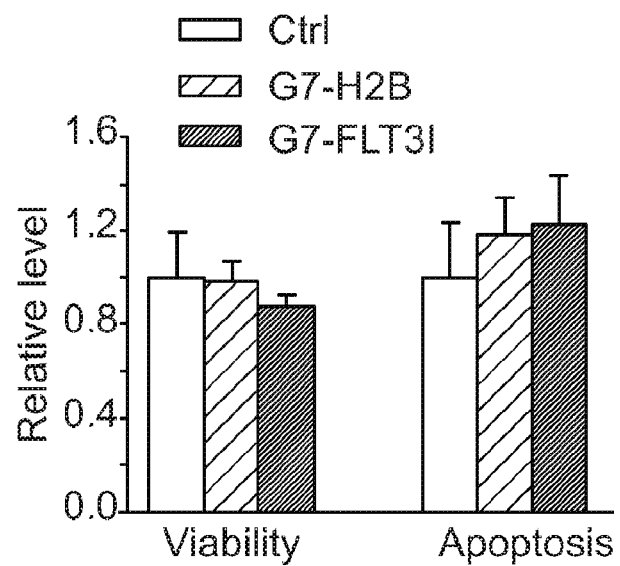
Figure 7F:
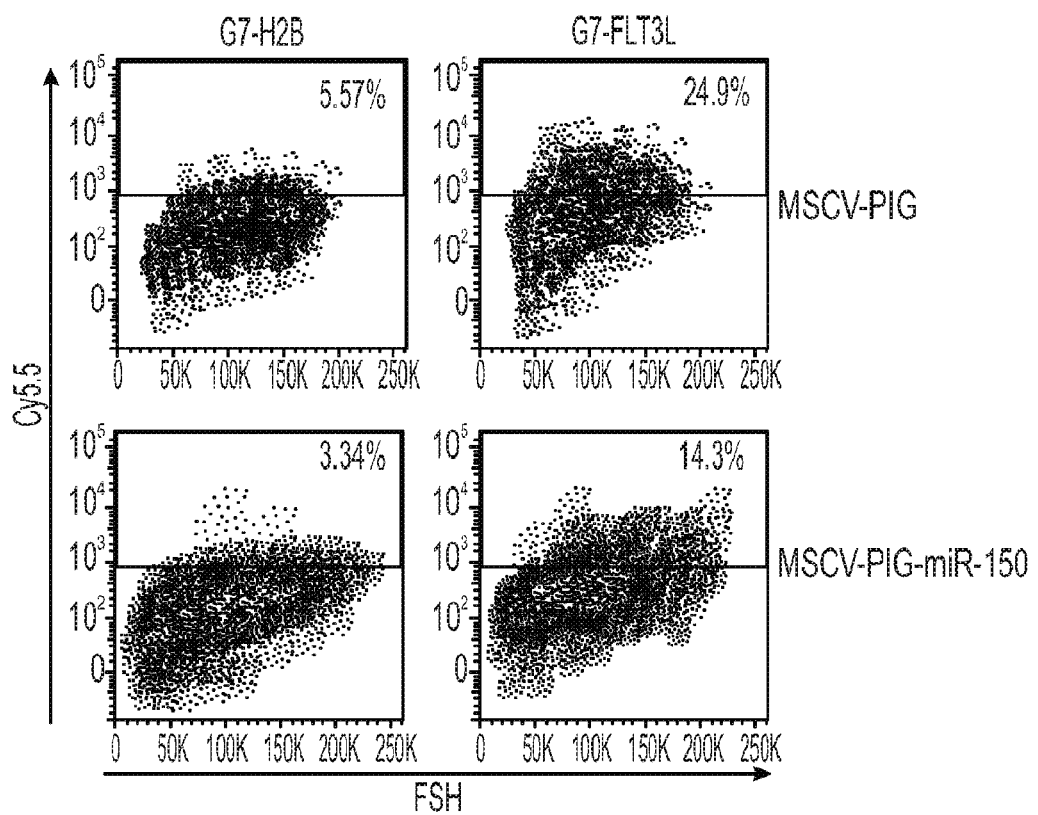
Figure 8A:
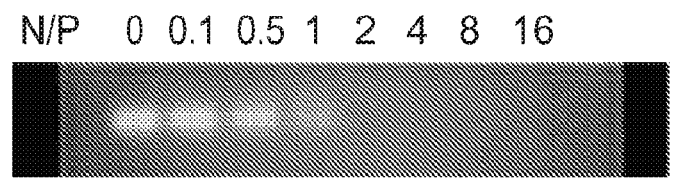
FIG. 8(A)-FIG. 8(D) demonstrate that G7 PAMAM dendrimers efficiently complex small, single stranded oligonucleotides.
Figure 8B:
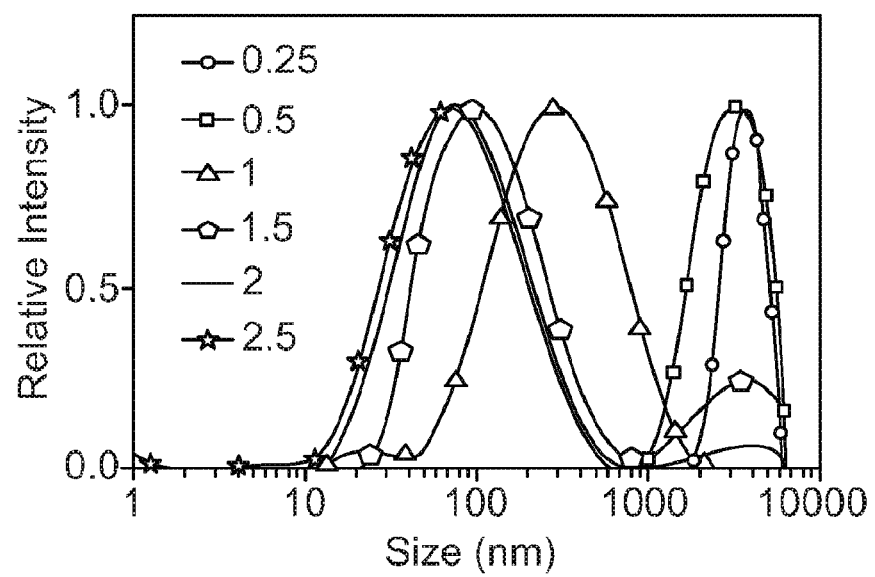
Figure 8C:
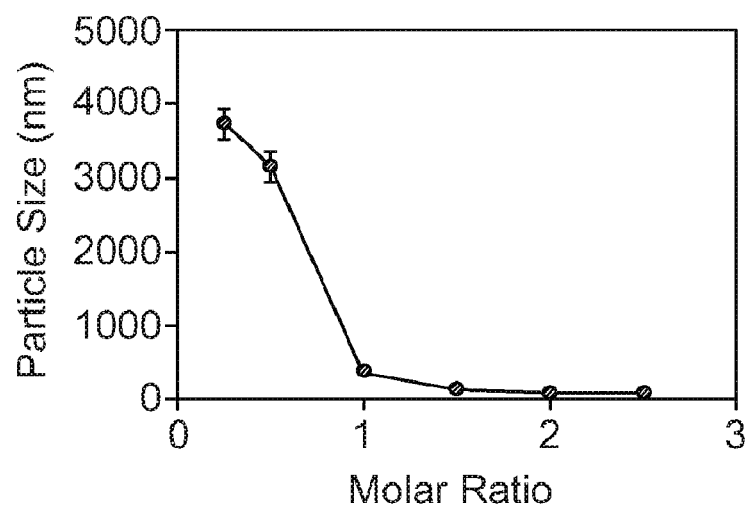
Figure 8D:
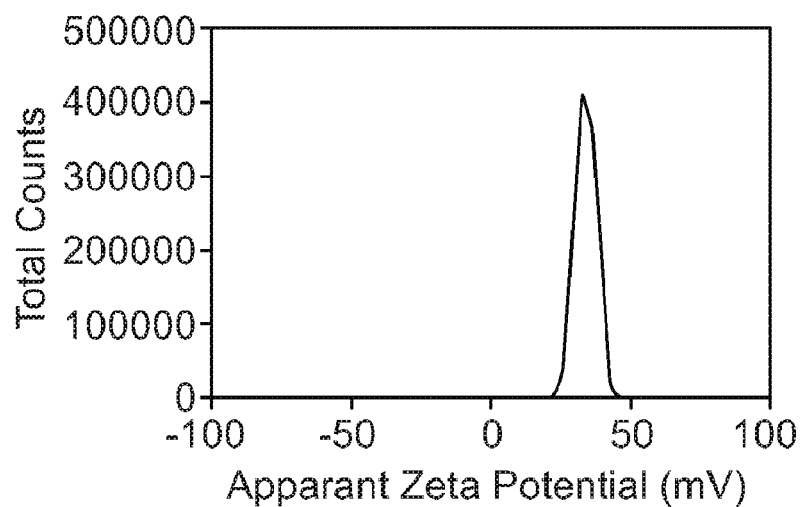

Whether the high level of FLT3 expression of target cells is required for the high uptake ratio of G7-FLT3L nanoparticles was thereafter determined. As reported previously, forced expression of miR-150 significantly reduced endogenous expression of FLT3. Suppression of endogenous FLT3 expression in MONOMAC-6 cells by overexpressing miR-150 resulted in a significant decrease of the uptake ratio of G7-FLT3L nanoparticles, but not that of G7-H2B nanoparticles (FIG. 2D; FIG. 7F). Neither G7-FLT3L nor G7-H2B dendrimers showed significant effects on the viability and apoptosis of MONOMAC-6 cells as compared with PBS, indicating low, if any, cytotoxicity of both dendrimer constructs (FIG. 2E).

Collectively, the above results indicate that G7-FLT3L nanoparticles can rapidly, efficiently, and selectively target FLT3-overexpressing AML cells, with minimal non-specific cellular toxicity.

Example 3

Figure 3A:
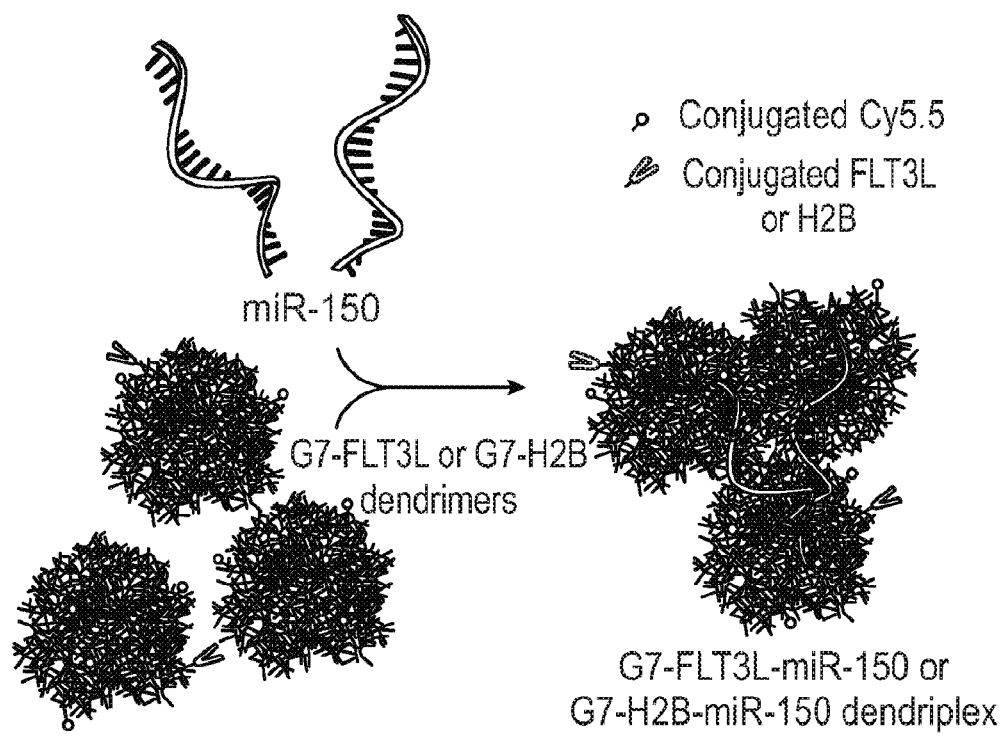
FIG. 3(A)-FIG. 3(H) shows the formation of the G7-FLT3L-miR-150 nanoparticles and their inhibitory effect on MONOMAC-6 cell growth, as well as the FLT3 signaling pathway in vitro.
Figure 3B:
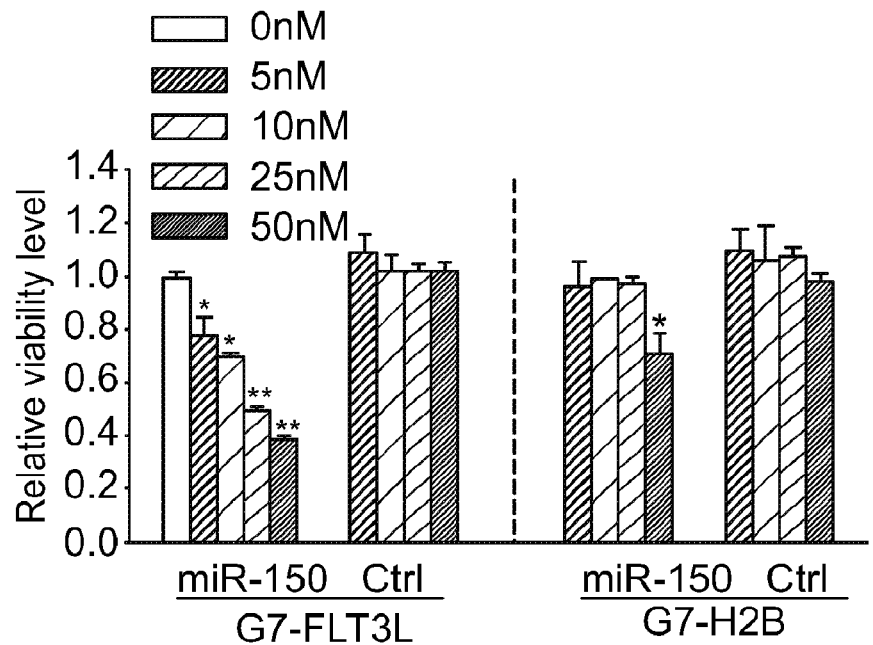
Figure 3C:
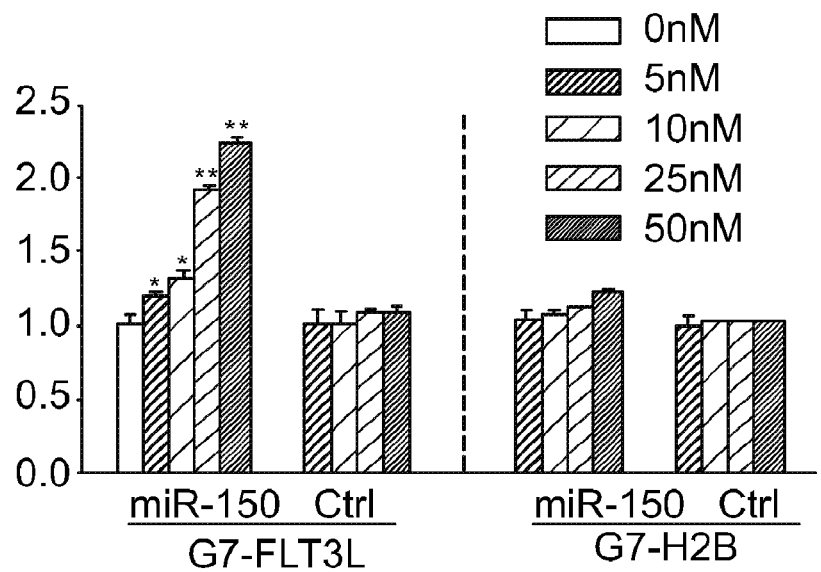
Figure 3D:
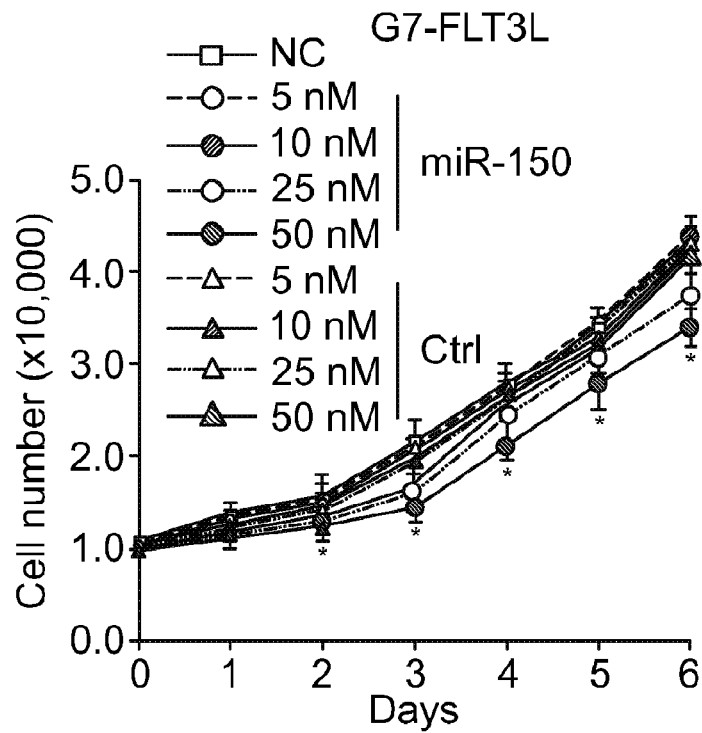
Figure 3E:
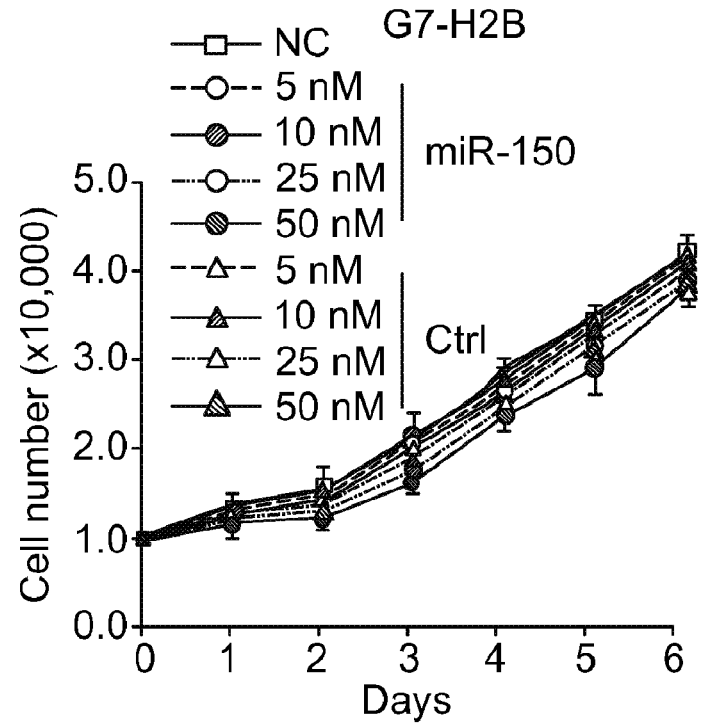

G7-FLT3L-miR-150 Nanoparticles Significantly Inhibit Viability/Proliferation and Enhance Apoptosis of FLT3-Overexpressing AML Cells.

miR-150 oligo was then integrated with G7-FLT3L dendrimers to form G7-FLT3L-miR-150 dendriplexes (FIG. 3A and FIG. 8). G7-FLT3L-miR-150 significantly reduced the viability and increased the apoptosis of MONOMAC-6 cells in a dose-dependent manner, while G7-H2B-miR-150 showed mild effects only at a high concentration (FIGS. 3B and 3C). Neither G7-FLT3L-control nor G7-H2B-control carrying miR-150 mutant control oligos (i.e., Control/Ctrl, which has a mutated "seed" sequence (i.e., mutations in the $2^{nd}$-$6^{th}$ nucleotides at the 5' end), as a specific loss-of-function control for the wild type miR-150) exhibited significant influence (FIGS. 3B and 3C). G7-FLT3L-miR-150 also remarkably inhibited AML cell proliferation even at a dose as low as 10 nM (FIG. 3D), while G7-H2B-miR-150 showed no significant inhibitory effects on the cell growth (FIG. 3E).

Figure 3F:
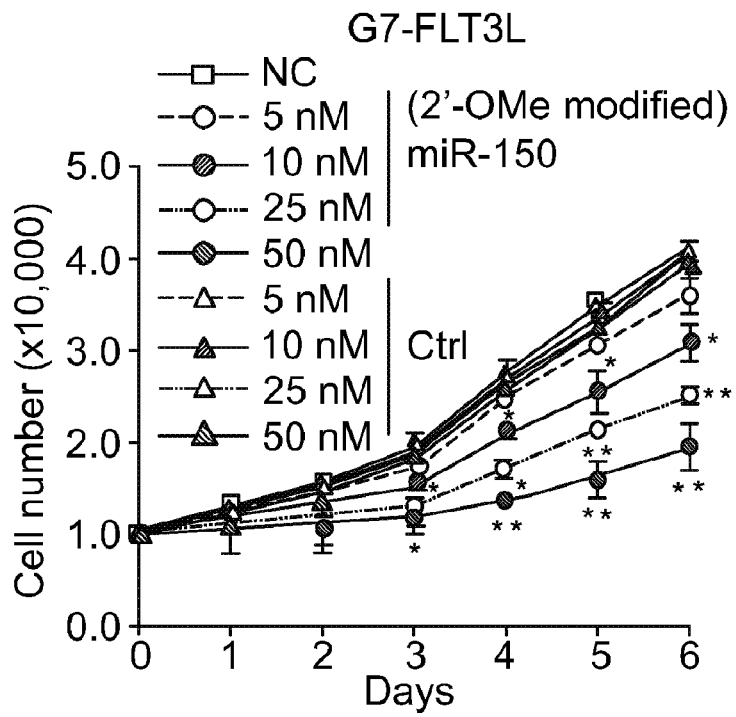
Figure 3G:
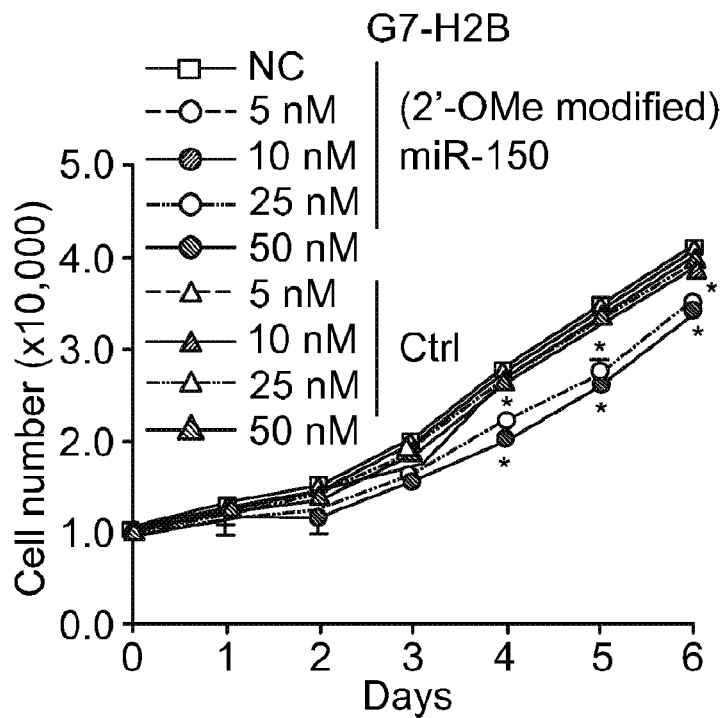

One problem observed with the G7-FLT3L-miR-150 nanoparticles, however, was that their inhibitory effect on cell growth was not sustained. Cells treated with even the highest dose of G7-FLT3L-miR-150 tended to grow at a normal speed 4 days post-treatment (FIG. 3D). To increase the stability of miR-150 oligos, a 2'-o-methyl (2'-OMe) modification (Lennox K A, et al. *Pharm Res.* 2010; 27:1788-99, incorporated herein by reference) was incorporated into the miRNA oligos. The G7-FLT3L nanoparticles carrying modified miR-150 exhibited a more sustained inhibition on cell growth (FIG. 3F). G7-H2B nanoparticles carrying 2'-OMe modified miR-150 showed a slight inhibitory effect at higher doses (FIG. 3G). Because 2'-OMe modified miR-150 oligos exhibited a more stable and potent effect than unmodified oligos, the modified oligos were employed in all subsequent studies.

Figure 3H:
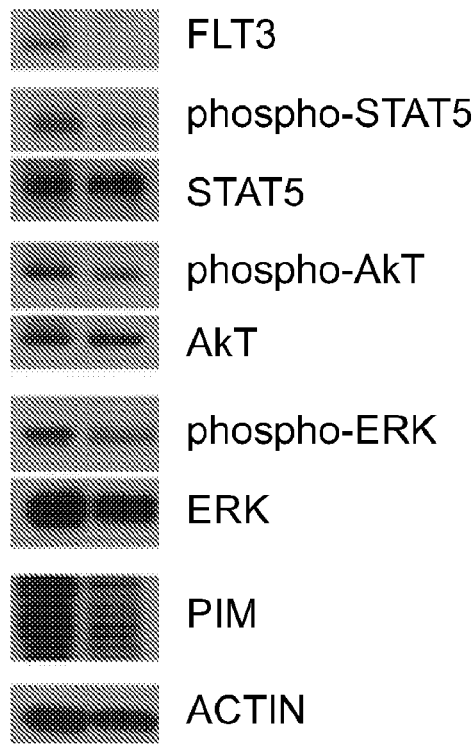
Figure 9:
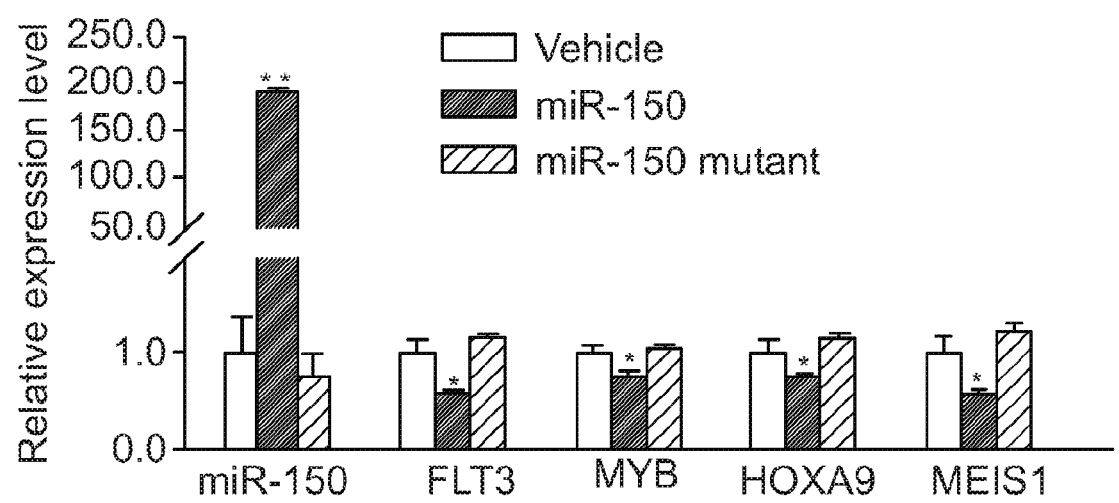
FIG. 9 sets forth a bar graph showing that G7-FLT3L-miR-150 nanoparticles repressed expression of direct or indirect target genes of miR-150 in vitro. MONOMAC-6 cells were treated with G7-FLT3L nanoparticles carrying 2'-OMe-modified miR-150 oligos (i.e., miR-150) or miR-150 mutant oligos (i.e., miR-150 mutant) at 50 nM, or with G7-FLT3L nanoparticles without oligos (i.e., vehicle) at 50 nM. 48 hrs after drug treatment, RNAs were collected and the expression levels of miR-150, FLT3, MYB, HOXA9 and MEIS1 are shown. FLT3 and MYB are direct targets of miR-150 while HOXA9 and MEIS1 are indirect targets of miR-150 (1-3). Note: As the Taqman qPCR kit for miR-150 cannot detect the miR-150 mutant, cells treated with miR-150 mutant oligos showed a similar level of miR-150 expression (i.e., the endogenous expression level) as cells received vehicle treatment as detected by Taqman qPCR. *, P<0.05; **, P<0.01.

The increase of intracellular miR-150 level in cells treated with G7-FLT3L-miR-150 resulted in a significant down-regulation of miR-150's direct or indirect target genes, including FLT3, MYB, HOXA9 and MEIS1 (FIG. 9), as well as a significant repression on FLT3 level, which in turn, led to the suppression of the FLT3 signaling pathway (see, e.g. Daver N, et al. *Blood.* 2015; 125:3236-45, incorporated herein by reference), featured with reduced activation of ERK, AKT and STATS, and down-regulation of PIM (FIG. 3H).

Example 4

Therapeutic Efficacy of G7-Flt3L-miR-150 Nanoparticles In Vivo

Figure 10A:
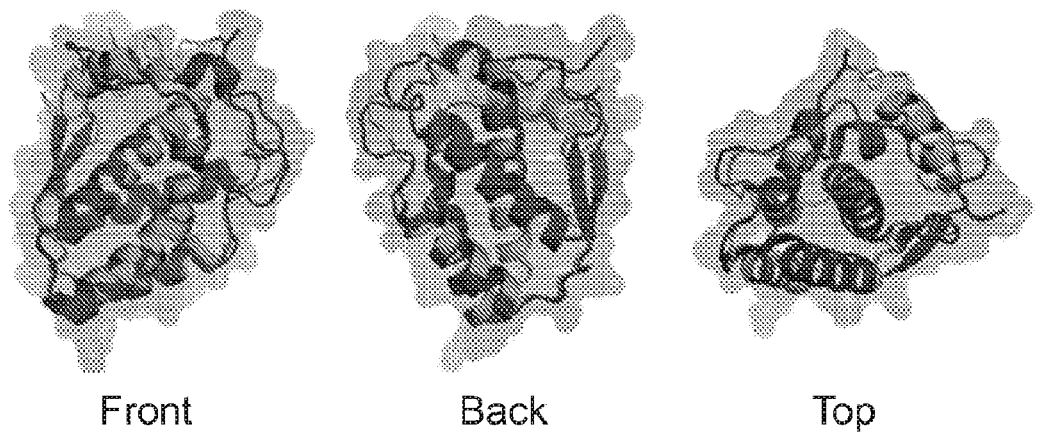
Figure 10B:
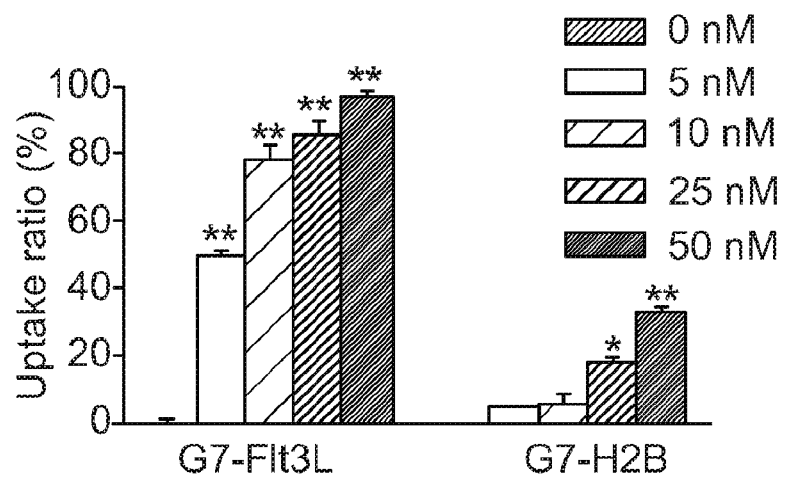
FIG. 10(B) MONOMAC-6 cells were treated with Cy5.5-conjugated G7-Flt3L or G7-H2B nanoparticles for 24 hrs at the indicated doses. The proportion of Cy5.5$^+$ cells were detected through flow cytometry analysis.
Figure 10C:
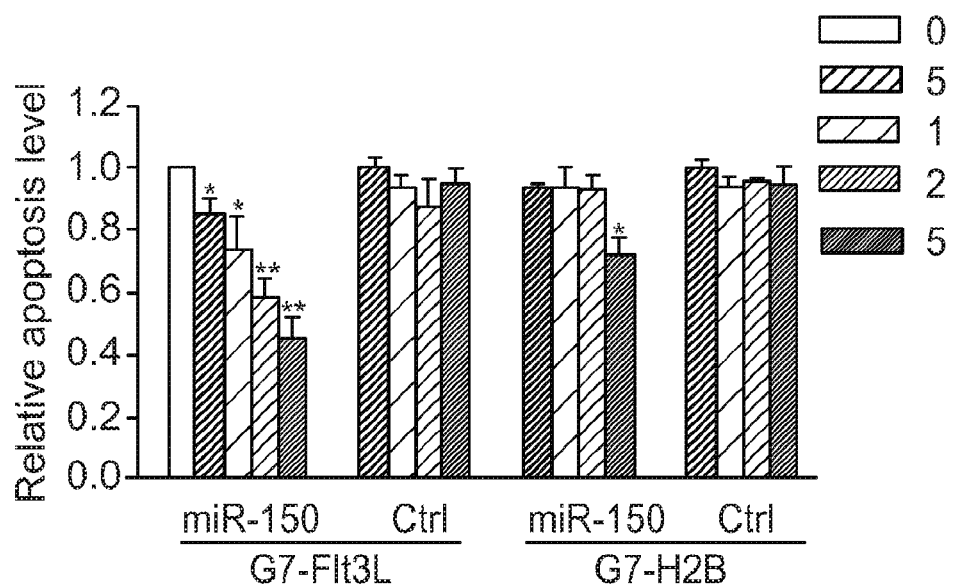
FIG. 10(C) shows cell viability for MONOMAC-6 cells treated with G7-Flt3L or G7-H2B nanoparticles complexed with miR-150 or miR-150 mutant RNA (i.e., Control/Ctrl) oligos at the indicated doses 48 hours post-treatment.
Figure 10D:
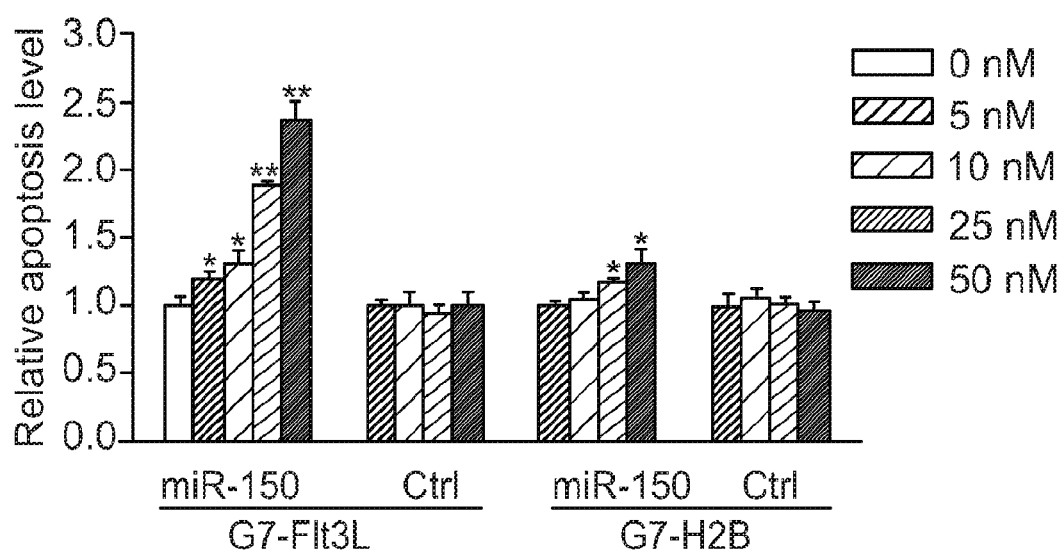
FIG. 10(D) shows apoptosis for MONOMAC-6 cells treated with G7-Flt3L or G7-H2B nanoparticles complexed with miR-150 or miR-150 mutant RNA (i.e., Control/Ctrl) oligos at the indicated doses 48 hrs post treatment.

The anti-leukemia effect of G7-Flt3L-miR-150 nanoparticles in treating AML in vivo was investigated. To reduce the cost and the size of the guiding molecule, synthetic peptides containing the major functional domains of soluble Flt3L protein rather than the entire soluble FLT3L (see FIG. 10A) were used. The new G7-Flt3L dendrimers exhibited a similar high uptake ratio and similar effects on inhibiting viability and promoting apoptosis (FIGS. 10B,C,D) as compared with the original G7-FLT3L dendrimers (FIG. 2B; FIG. 3B,C).

Figure 4A:
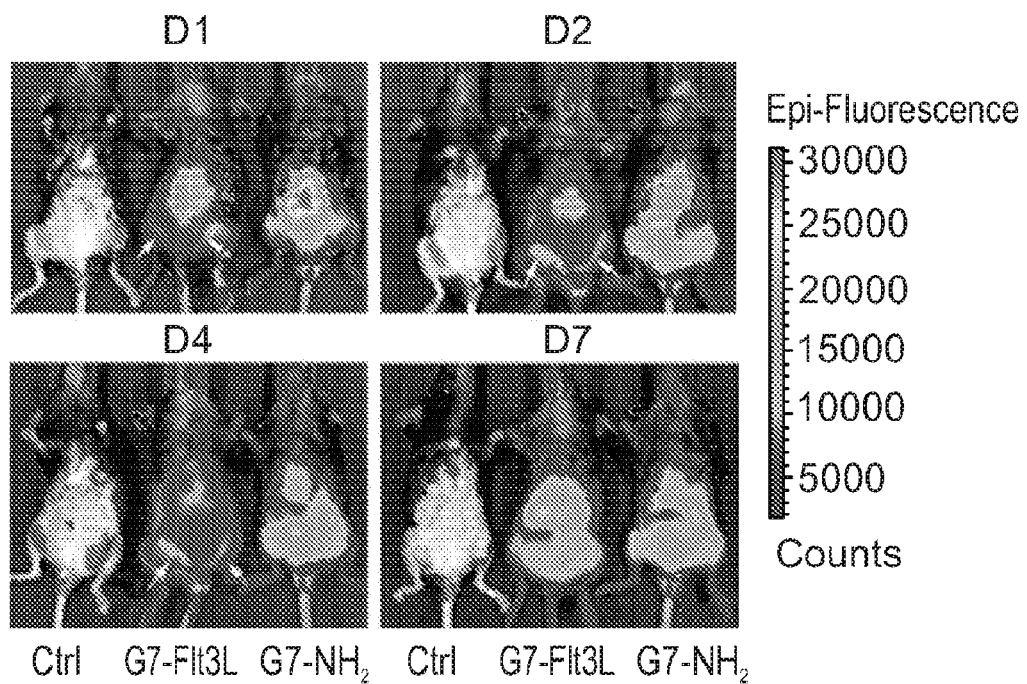
FIG. 4(A)-FIG. 4(C) shows in vivo distribution of the G7-Flt3L or G7-NH$_2$.
Figure 4B:
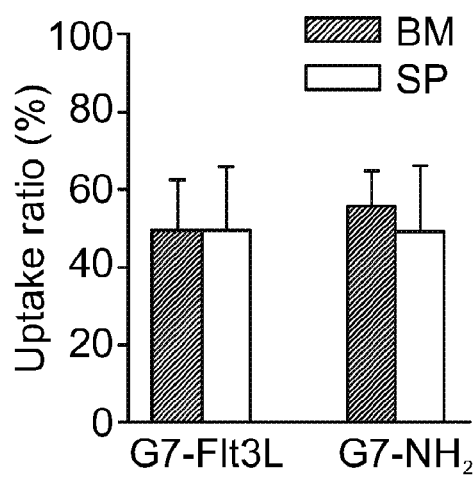
Figure 4C:
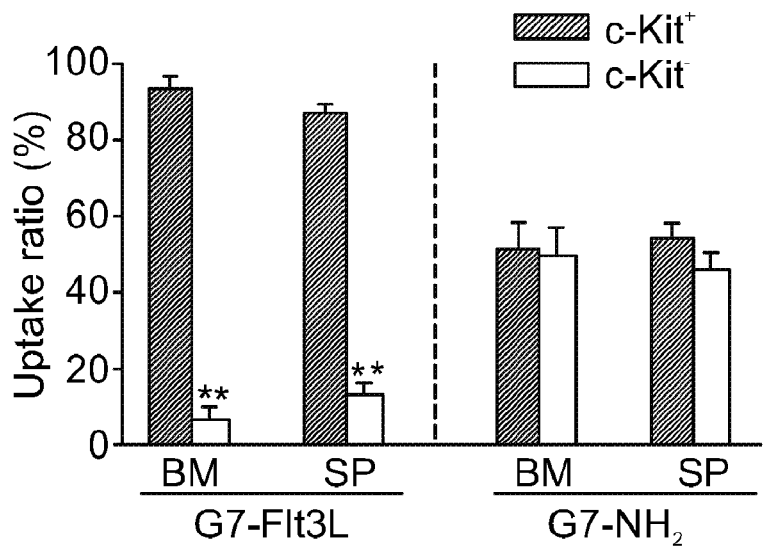
Figure 11A:
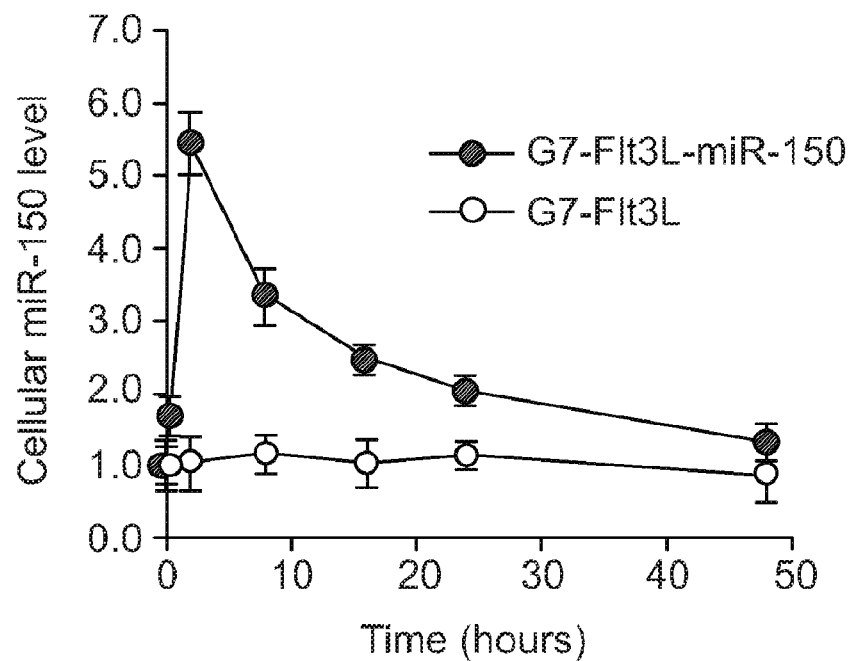
FIG. 11(A)-FIG. 11(B) shows in vivo uptake and function of G7-Flt3L-miR-150 nanoparticles.

To demonstrate the in vivo distribution of the nanoparticles, the G7-Flt3L or control nanoparticles were injected into normal mice. Whole animal imaging shows different distributions of the two nanoparticles: G7-Flt3L was mainly enriched in the bone marrow and the liver, while G7-NH$_2$ showed a more diffuse distribution all over the abdomen (FIG. 4A). Both nanoparticles were taken up at a similar ratio in the bone marrow and the spleen of the injected mice, but more G7-Flt3L$^+$ cells are c-Kit$^+$ progenitor cells, indicating a preferential recruitment of the G7-Flt3L nanoparticles to leukemic stem cells or progenitors with overexpressed Flt3 (FIGS. 4B and 4C). The level of miR-150 was detected in mouse BM c-Kit$^+$ cells from 30 minutes to 48 hours after a single dosage of G7-Flt3L-miR-150. Results showed that the cellular level of miR-150 was maintained at 2.01 folds of the control group 24 hours post-treatment, and at 1.32 folds 48 hours post-treatment (FIG. 11A).

Figure 5A:
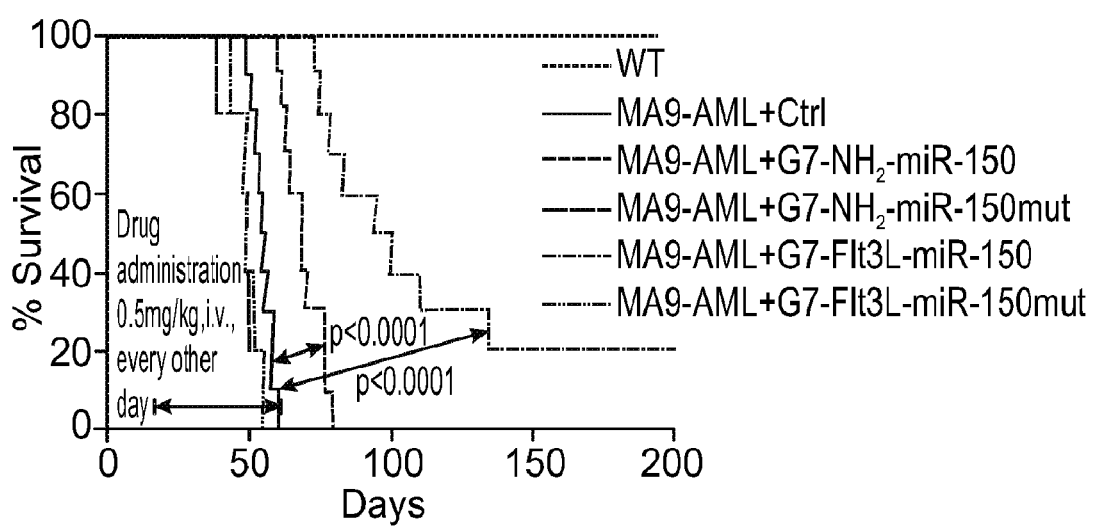
FIG. 5(A)-FIG. 5(C) show the therapeutic effect of G7-Flt3L-miR-150 nanoparticles in treating AML.
Figure 5B:
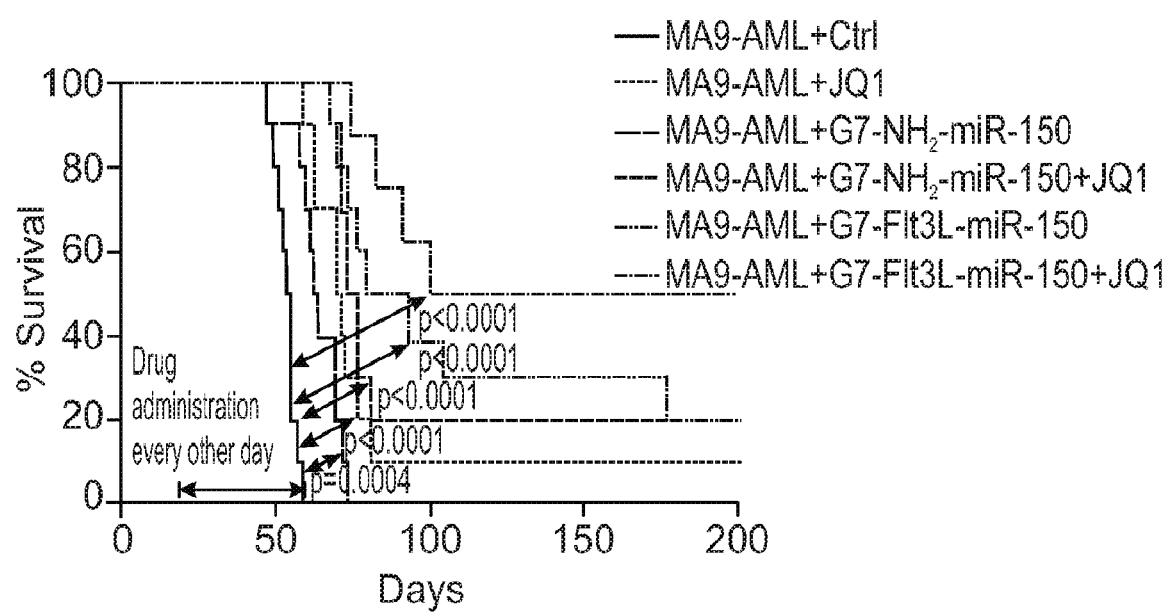
Figure 5C:
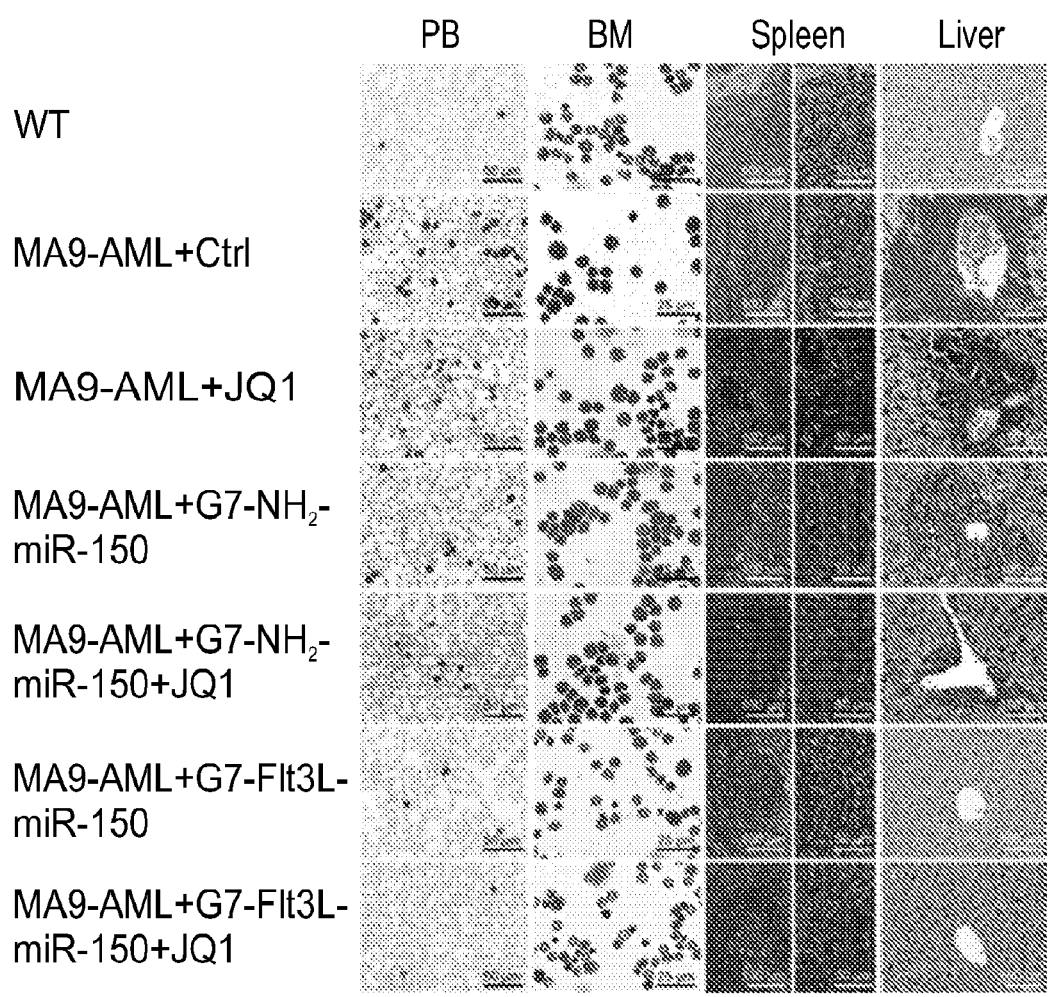
Figure 11B:
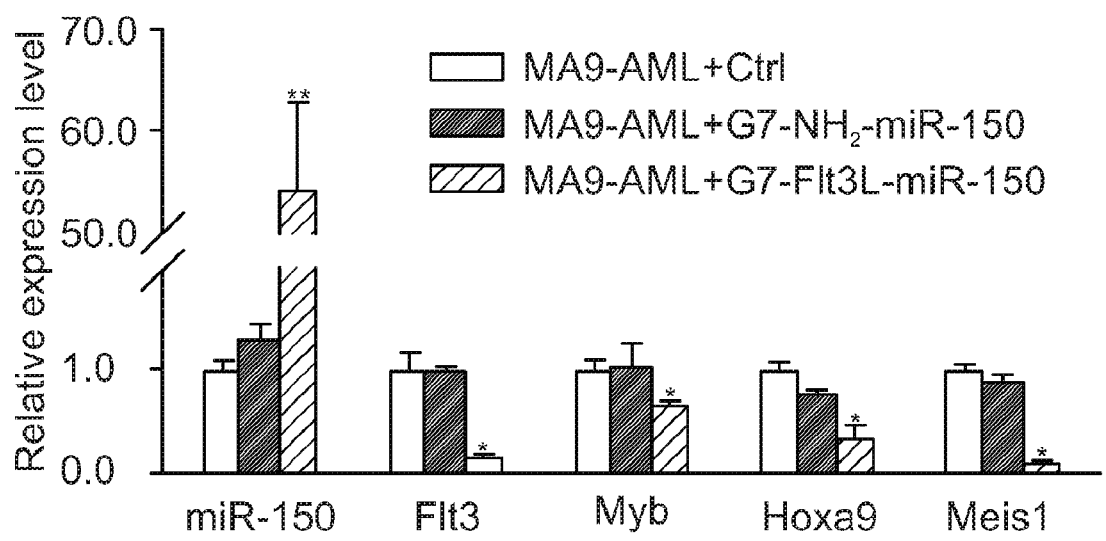
Figure 12:
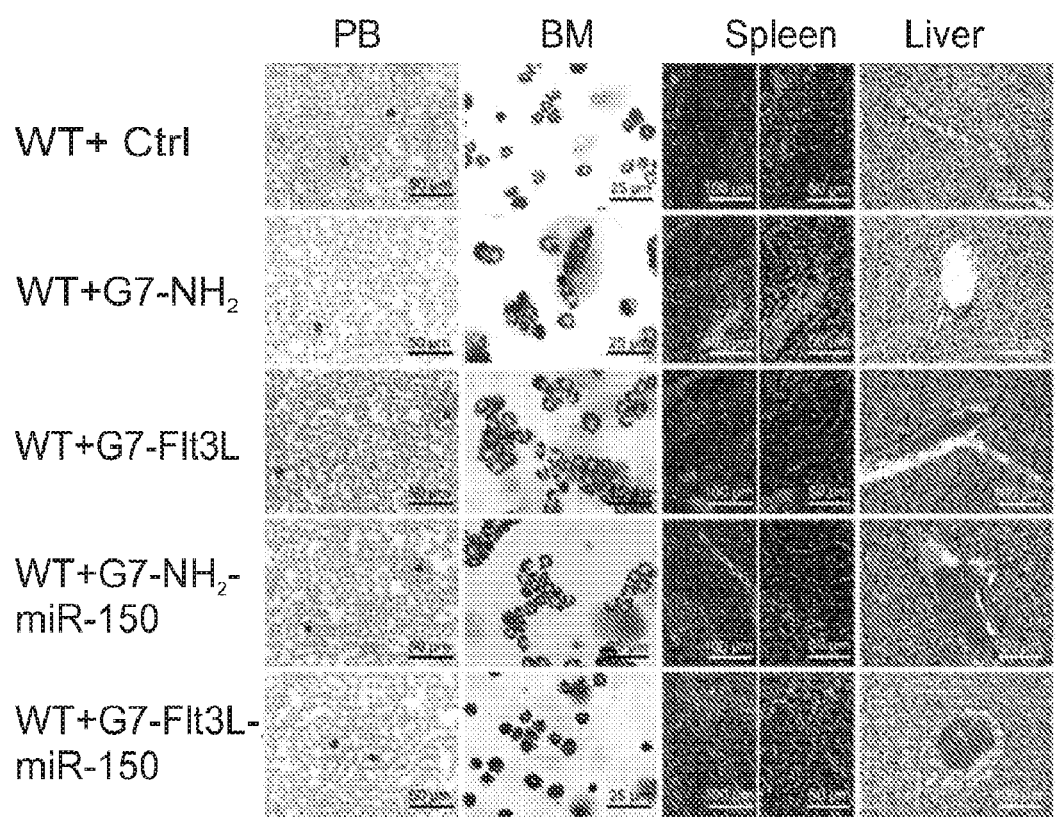
FIG. 12 provides an analysis of the potential influence of the nanoparticles on hematopoietic system in normal mice, C57BL/6 wild type mice were treated with 0.5 mg/kg PBS (Control/Ctrl), G7-NH$_2$, G7-Flt3L, G7-NH$_2$-miR-150 or G7-Flt3L-miR-150, i.v., every other day, for ten times. Mice were sacrificed 12 weeks after the last administration, subsequent Wright-Giemsa stained PB and BM, and H&E stained spleen and liver of the animals are shown.

The in vivo therapeutic effects of the miR-150 nanoparticles were also investigated in a MLL-rearranged leukemic mouse model. G7-Flt3L-miR-150 nanoparticles showed the best therapeutic effect as compared with the control group or the G7-NH$_2$-miR-150 treated group, while miR-150-mutant nanoparticles showed no anti-leukemia effect (FIG. 5A). Notably, G7-Flt3L-miR-150 treatment almost completely blocked MLL-AF9-induced leukemia in 20% of the mice. The therapeutic effect of G7-Flt3L-miR-150 was also evidenced by the morphological changes in peripheral blood (PB), bone marrow (BM), spleen and liver between the treated mice and control AML mice (FIG. 5C). The anti-leukemia effect of G7-Flt3L-miR-150 nanoparticles is associated with a significant increase in intracellular miR-150 level and decrease in the expression of miR-150's critical direct targets (e.g., Flt3 and Myb) and indirect targets (e.g., Hoxa9 and Meis1) (FIG. 11B). Furthermore, neither G7-Flt3L-miR-150 nor G7-NH$_2$-miR-150 nanoparticles exhibited noticeable effects on normal hematopoiesis (Table 2; FIG. 12).

TABLE 2

Effects of the nanoparticles on mouse blood cell differentiation two (A) or four (B) weeks after the last administration of nanoparticles or control (PBS)

| | WBC (K/μl) | NE (K/μl) | LY (K/μl) | MO (K/μl) | EO (K/μl) | BA (K/μl) | RBC (M/μl) | PLT (K/μl) |
|---|---|---|---|---|---|---|---|---|
| (A) Two weeks after the last administration of nanoparticles or control (PBS) | | | | | | | | |
| 2 W | | | | | | | | |
| PBS | 7.42 ± 1.02 | 1.63 ± 0.48 | 5.39 ± 0.66 | 0.29 ± 0.02 | 0.08 ± 0.09 | 0.03 ± 0.04 | 9.42 ± 0.94 | 874.5 ± 38.9 |
| G7-NH$_2$ | 6.67 ± 1.56 | 1.49 ± 0.42 | 4.9 ± 1.2 | 0.15 ± 0.01 | 0.02 ± 0.02 | 0.01 ± 0.0 | 9.12 ± 0.78 | 728.5 ± 263.75 |
| G7-NH$_2$-miR-150 | 7.55 ± 0.68 | 1.74 ± 0.16 | 5.21 ± 0.67 | 0.42 ± 0.18 | 0.14 ± 0.03 | 0.05 ± 0.02 | 9.5 ± 0.46 | 719 ± 195.16 |
| G7-Flt3L | 7.25 ± 1.94 | 1.83 ± 0.83 | 4.89 ± 0.76 | 0.36 ± 0.31 | 0.13 ± 0.04 | 0.04 ± 0.0 | 8.23 ± 1.26 | 740 ± 210.71 |
| G7-Flt3L-miR-150 | 6.57 ± 0.6 | 1.05 ± 0.04 | 5.28 ± 0.73 | 0.19 ± 0.02 | 0.04 ± 0.04 | 0.01 ± 0.01 | 7.18 ± 2.23 | 768 ± 115.97 |
| Normal range | 1.8-10.7 | 0.1-2.4 | 0.9-9.3 | 0.0-0.4 | 0.0-0.2 | 0.0-0.2 | 6.36-9.42 | 592-2972 |
| (B) Four weeks after the last administration of nanoparticles or control (PBS) | | | | | | | | |
| 4 W | | | | | | | | |
| PBS | 6.56 ± 3.42 | 1.1 ± 0.74 | 5.03 ± 2.34 | 0.39 ± 0.38 | 0.04 ± 0.02 | 0.01 ± 0.0 | 8.73 ± 0.97 | 1097.5 ± 219.9 |
| G7-NH$_2$ | 6.48 ± 2.14 | 1.01 ± 0.51 | 5.1 ± 1.75 | 0.33 ± 0.12 | 0.02 ± 0.01 | 0.01 ± 0.01 | 7.47 ± 0.31 | 952.5 ± 74.25 |
| G7-NH$_2$-miR-150 | 6.61 ± 0.12 | 0.81 ± 0.29 | 5.49 ± 0.21 | 0.29 ± 0.04 | 0.01 ± 0.01 | 0.0 ± 0.0 | 7.3 ± 0.36 | 1112.5 ± 284.96 |
| G7-Flt3L | 7.2 ± 2.75 | 1.52 ± 0.81 | 5.29 ± 1.88 | 0.29 ± 0.05 | 0.05 ± 0.05 | 0.02 ± 0.01 | 7.61 ± 0.37 | 930.5 ± 9.19 |

TABLE 2-continued

Effects of the nanoparticles on mouse blood cell differentiation two (A) or four (B) weeks after the last administration of nanoparticles or control (PBS)

|  | WBC (K/μl) | NE (K/μl) | LY (K/μl) | MO (K/μl) | EO (K/μl) | BA (K/μl) | RBC (M/μl) | PLT (K/μl) |
|---|---|---|---|---|---|---|---|---|
| G7-Flt3L-miR-150 | 7.1 ± 1.26 | 1.47 ± 0.07 | 5.16 ± 1.39 | 0.3 ± 0.01 | 0.12 ± 0.0 | 0.06 ± 0.04 | 7.79 ± 0.25 | 929 ± 21.21 |
| Normal range | 1.8-10.7 | 0.1-2.4 | 0.9-9.3 | 0.0-0.4 | 0.0-0.2 | 0.0-0.2 | 6.36-9.42 | 592-2972 |

Note:
Normal C57BL/6 mice were treated with 0.5 mg/kg PBS (control), G7-NH$_2$, G7-Flt3L, G7-NH$_2$-miR-150 or G7-Flt3L-miR-150 nanoparticles every other day for 20 days.
Shown are data collected at the indicated time points (i.e. 2 weeks (A) or 4 weeks (B)) post the last i.v. injection of the nanoparticles or PBS.
WBC = white blood cells; NE = neutrophils; LY = lymphocytes; MO = monocytes; EO = eosinophils; BA = basophils; RBC = red blood cells; PLT = platelets.
Means ± Standard deviations are shown.

Example 5

Co-Administration of a BET Inhibitor.

JQ1 is a small-molecule inhibitor of BET bromodomains and has been proven to be effective in repressing MLL-AF9/Nras$^{G12D}$-induced AML progression in vivo (Zuber J, et al. Nature. 2011; 478:524-8, incorporated herein by reference). Since MYC is also a downstream target of FLT3, the question of whether the combination of miR-150 nanoparticles and JQ1 exhibits a stronger therapeutic effect than each alone was investigated. The animal leukemia model studies showed that JQ1 alone and G7-Flt3L-miR-150 nanoparticles alone significantly ($P<0.0001$) extended the median survival of MLL-AF9 AML mice from 54 days (Ctrl; PBS treated) to 69.5 and 86 days, respectively, while their combination substantially extended the median survival to >150 days, suggesting a synergistic effect between JQ1 and miR-150 nanoparticles in treating FLT3-overexpressing AML (FIG. 5B). Notably, 50% of the leukemic mice treated with this combination survived for more than 200 days (FIG. 5B) and their pathological morphologies in PB, BM, spleen and liver tissues became normal (FIG. 5C). JQ1 and G7-Flt3L-miR-150, each alone or in combination, did not cause any noticeable side effects on normal hematopoiesis in vivo (Table 3).

Example 6

Figure 6A:
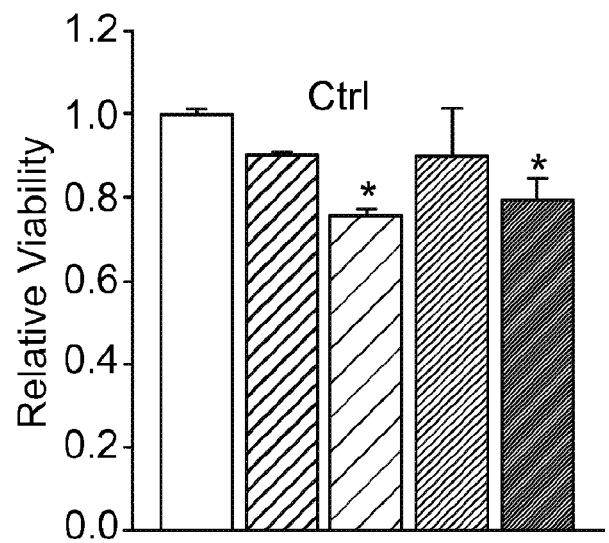
FIG. 6(A)-FIG. 6(M) show the broad inhibitory effects of G7-Flt3L-miR-150 nanoparticles on AML cell viability.
Figure 6B:
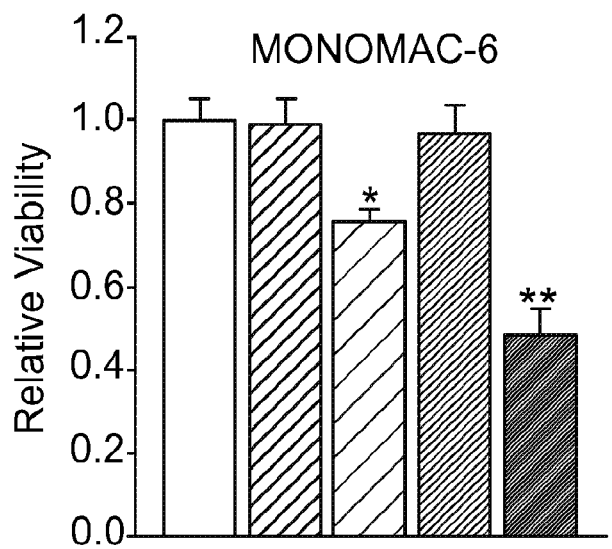
Figure 6C:
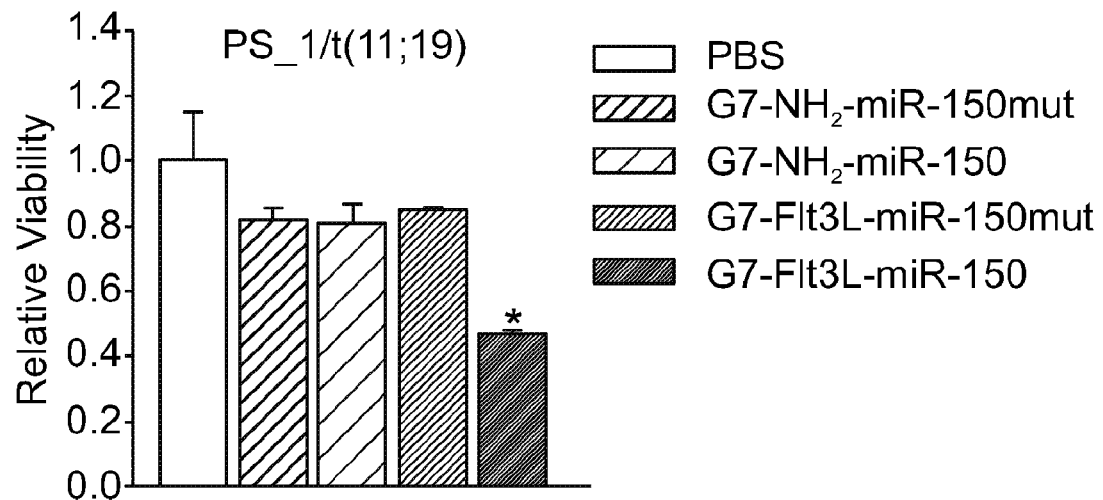
Figure 6D:
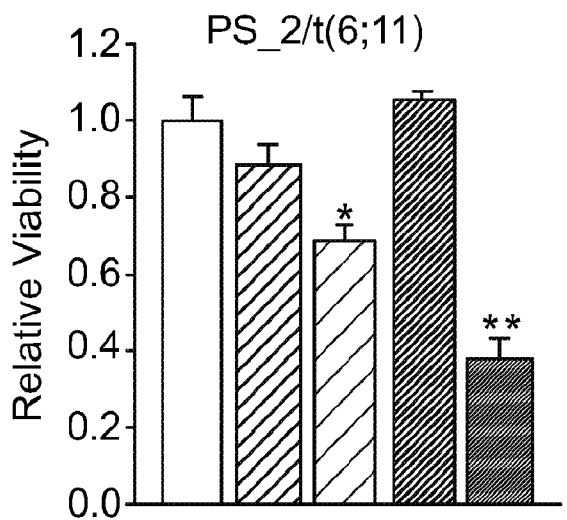
Figure 6E:
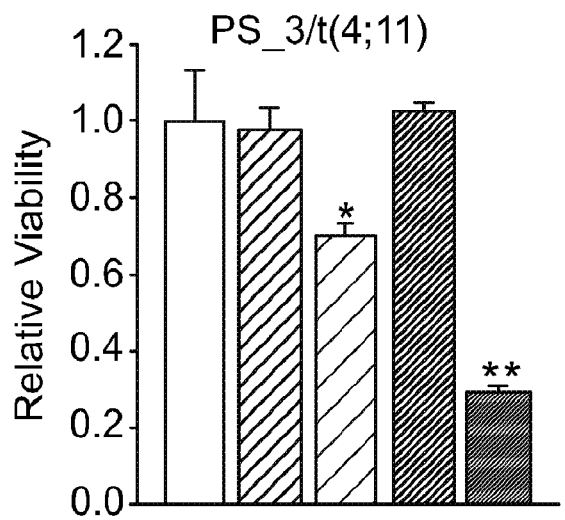
Figure 6F:
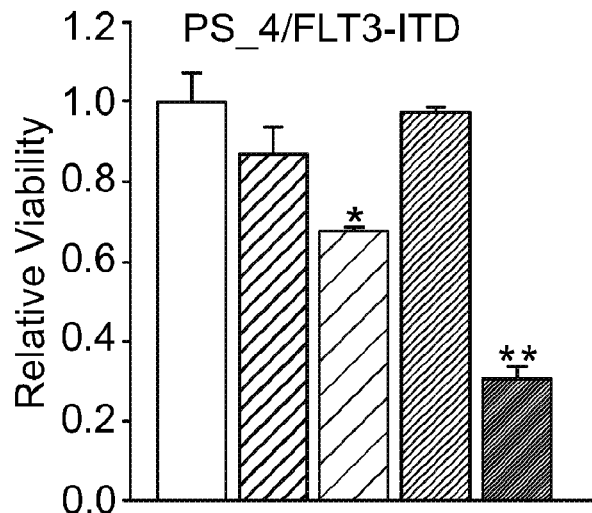
Figure 6G:
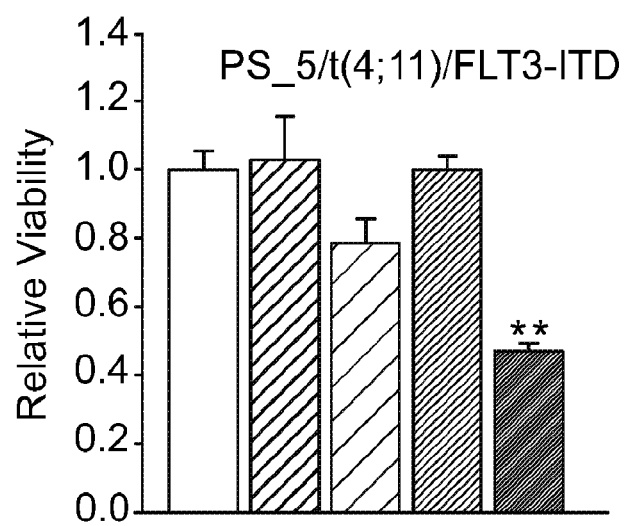
Figure 6H:
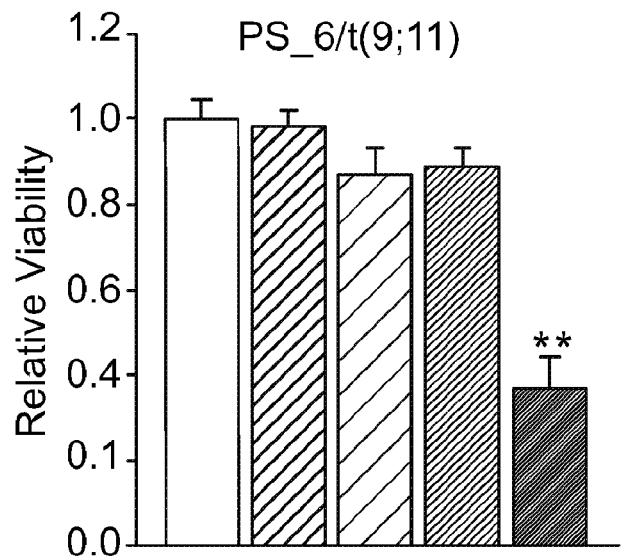
Figure 6I:
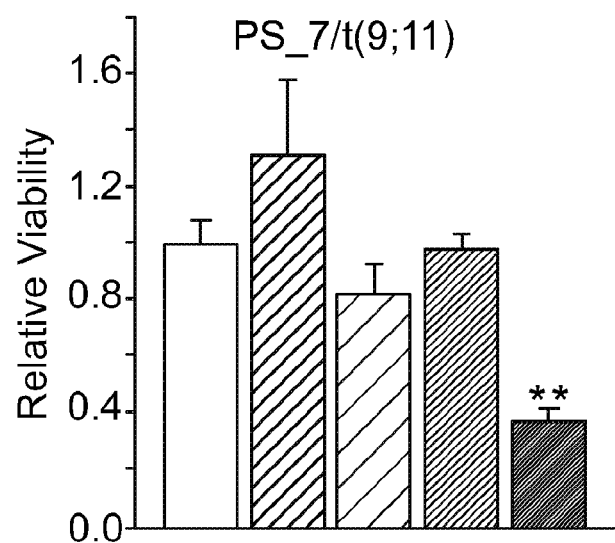
Figure 6J:
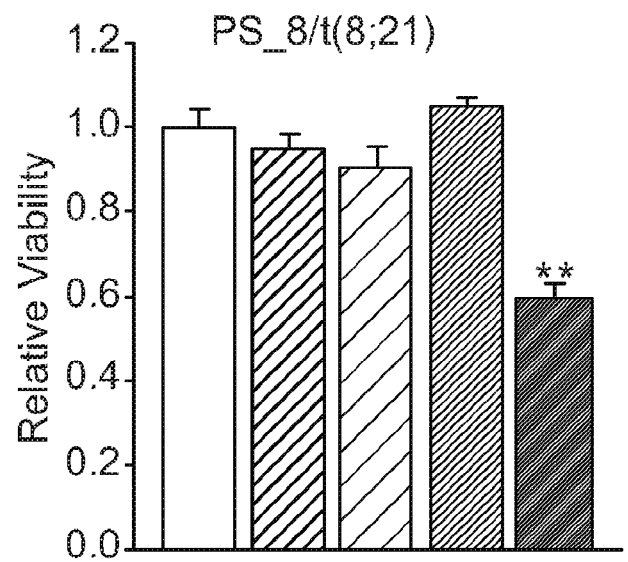
Figure 6K:
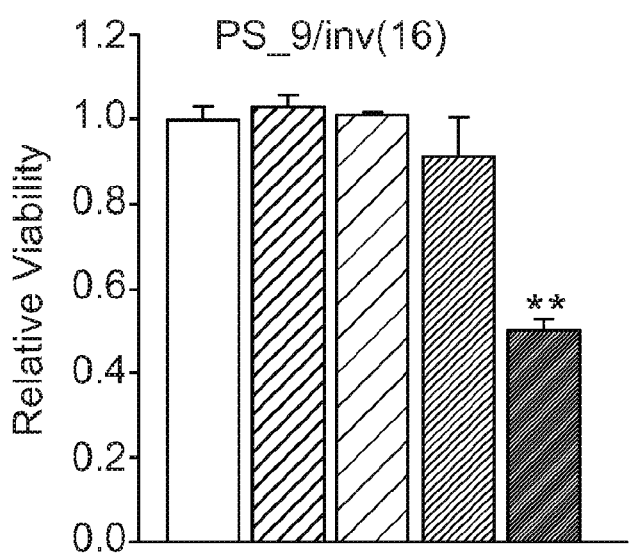
Figure 6L:
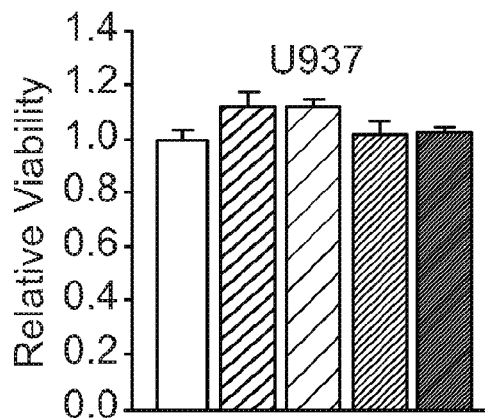
Figure 6M:
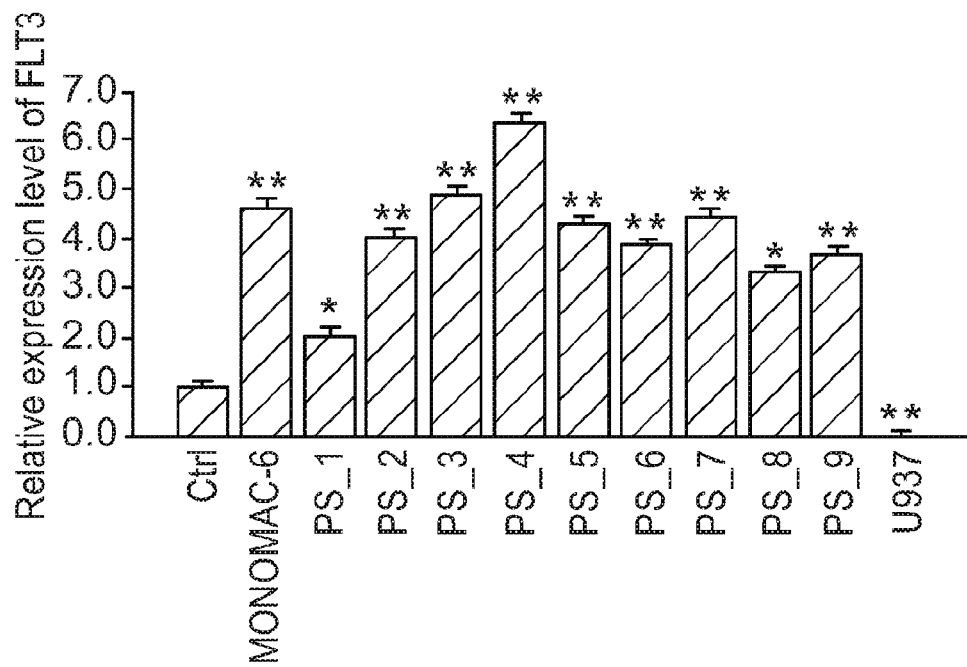

The Broad Anti-Leukemic Effect of G7-Flt3L-miR-150 Nanoparticles on Various Subtypes of Human AMLs AML cell lines and primary patient samples carrying various cytogenetic or molecular abnormalities were treated with an embodiment of the inventive nanoparticles. While exhibiting very minor inhibitory effect on the viability of normal control mononuclear cells from healthy donors (Control/Ctrl), G7-Flt3L-miR-150 nanoparticles exhibited a significant inhibitory effect on the viability of leukemic mononuclear BM blast cells collected from nine primary AML patients carrying t(11;19)/MLL-ENL, t(6;11)/MLL-AF6, t(4;11)/MLL-AF4, FLT3-ITD, t(4;11)/FLT3-ITD, t(9;11)/MLL-AF9, t(8;21)/AML1-ETO or inv(16)/CBFB-MYH11, to a degree similar to that of MONOMAC-6 cells, or even better (FIGS. 6A-6K). In contrast, no inhibitory effect was observed on the viability of U937 cells (FIG. 6L). The sensitivity/receptivity of the AML cells to G7-Flt3L-miR-150 nanoparticle treatment seems to be related to the expression level of endogenous FLT3 in the cells (FIG. 6M). As expected, only the nanoparticles with both Flt3L guiding peptides and functional miR-150 oligos exhibited a potent and selective inhibitory effect on FLT3-overexpressing AML cells. Taken together, these results indicate that G7-Flt3L-miR-150 nanoparticles exhibit a broad anti-leukemic effect by selectively targeting a variety of AML subtypes with overexpression of FLT3.

TABLE 3

Effects of JQ1 and/or miR-150 nanoparticles on mouse blood cell differentiation four weeks after the last administration of drugs or control (PBS)

| 4 W | WBC (K/μl) | NE (K/μl) | LY (K/μl) | MO (K/μl) | EO (K/μl) | BA (K/μl) | RBC (M/μl) | PLT (K/μl) |
|---|---|---|---|---|---|---|---|---|
| PBS | 6.62 ± 0.84 | 1.28 ± 0.34 | 4.74 ± 0.72 | 0.39 ± 0.02 | 0.17 ± 0.079 | 0.04 ± 0.04 | 6.67 ± 1.01 | 844 ± 39.7 |
| JQ1 | 7.18 ± 0.76 | 1.2 ± 0.62 | 5.57 ± 0.83 | 0.36 ± 0.32 | 0.04 ± 0.04 | 0.01 ± 0.0 | 8.12 ± 1.13 | 688 ± 110.3 |
| JQ1 + G7-Flt3L-miR-150 | 7.28 ± 1.12 | 1.04 ± 0.07 | 5.81 ± 1.03 | 0.39 ± 0.08 | 0.03 ± 0.02 | 0.01 ± 0.01 | 8.49 ± 1.23 | 657 ± 112 |
| Normal range | 1.8-10.7 | 0.1-2.4 | 0.9-9.3 | 0.0-0.4 | 0.0-0.2 | 0.0-0.2 | 6.36-9.42 | 592-2972 |

Note:
Normal C57BL/6 mice were treated with 0.5 mg/kg PBS (control), 50 mg/kg JQ1, 0.5 mg/kg G7-Flt3L-miR-150 nanoparticles, or 50 mg/kg JQ1 plus 0.5 mg/kg G7-Flt3L-miR-150 nanoparticles, i.v., every day for 15 days.
Shown are data collected at the indicated time points (i.e. 4 weeks) post the last i.v. injection of the drugs or PBS.
WBC = white blood cells; NE = neutrophils; LY = lymphocytes; MO = monocytes; EO = eosinophils; BA = basophils; RBC = red blood cells; PLT = platelets.
Means ± Standard deviations are shown.

The invention claimed is:

1. A nanoparticle delivery system designed for sustained delivery of microRNA-150 (miR-150) to FLT3-overexpressing acute myeloid leukemia (AML) cells, the delivery system comprising poly(amidoamine) (PAMAM) dendrimers complexed with miR-150, wherein at least one dendrimer is surface-functionalized with a ligand specific for FLT3 receptor;
wherein the ligand specific for FLT3 receptor consists of a synthetic FLT3L peptide having at least 90% sequence homology to SEQ ID NO: 1.

2. The delivery system according to claim 1, wherein the PAMAM dendrimers comprise between generation-2 and generation-8 dendrimers.

3. The delivery system according to claim 1, wherein the PAMAM dendrimers comprise generation 7 (G7) dendrimers.

4. The delivery system according to claim 1 wherein the synthetic FLT3L peptide is Flt3L peptide consisting of SEQ ID NO: 1.

5. The delivery system according to claim 1, wherein the miR-150 is modified for stability.

6. The delivery system according to claim 5, wherein the miR-150 stability modification comprises 2'-O methylation.

7. The nanoparticle delivery system according to claim 1 comprising G7-Flt3L-(2'OMe)miR-150.

* * * * *

SEQUENCE LISTING

```
<160> NUMBER OF SEQ ID NOS: 3

<210> SEQ ID NO 1
<211> LENGTH: 74
<212> TYPE: PRT
<213> ORGANISM: Artificial Sequence
<220> FEATURE:
<223> OTHER INFORMATION: Synthetic Flt3L Peptide

<400> SEQUENCE: 1

Ser Ser Asn Phe Lys Val Lys Phe Arg Glu Leu Thr Asp His Leu Leu
1               5                   10                  15

Lys Asp Tyr Pro Val Thr Val Ala Val Asn Leu Gln Asp Glu Lys His
            20                  25                  30

Cys Lys Ala Leu Trp Ser Leu Phe Leu Ala Gln Arg Trp Ile Glu Gln
        35                  40                  45

Leu Lys Thr Val Ala Gly Ser Lys Met Gln Thr Leu Leu Glu Asp Val
    50                  55                  60

Asn Thr Glu Ile His Phe Val Thr Ser Cys
65                  70

<210> SEQ ID NO 2
<211> LENGTH: 22
<212> TYPE: RNA
<213> ORGANISM: Artificial Sequence
<220> FEATURE:
<223> OTHER INFORMATION: Synthetic miR-150 RNA oligonucleotide

<400> SEQUENCE: 2
ucucccaacc cuuguaccag ug                                            22

<210> SEQ ID NO 3
<211> LENGTH: 22
<212> TYPE: RNA
<213> ORGANISM: Artificial Sequence
<220> FEATURE:
<223> OTHER INFORMATION: Synthetic miR-150 mutant RNA oligonucleotide

<400> SEQUENCE: 3
uuauuuuacc cuuguaccag ug                                            22
```